United States Patent
Sing et al.

(10) Patent No.: US 7,037,323 B2
(45) Date of Patent: May 2, 2006

(54) PLEDGET-HANDLING SYSTEM AND METHOD FOR DELIVERING HEMOSTASIS PROMOTING MATERIAL TO A BLOOD VESSEL PUNCTURE SITE BY FLUID PRESSURE

(75) Inventors: Eduardo Chi Sing, Dana Point, CA (US); Luis Urquidi, Laguna Hills, CA (US); Mark Ashby, Laguna Niguel, CA (US); Andrew Cragg, Edina, MN (US)

(73) Assignee: Sub-Q, Inc., San Clemente, CA (US)

( * ) Notice: Subject to any disclaimer, the term of this patent is extended or adjusted under 35 U.S.C. 154(b) by 25 days.

(21) Appl. No.: 10/732,441

(22) Filed: Dec. 9, 2003

(65) Prior Publication Data
US 2004/0176723 A1 Sep. 9, 2004

Related U.S. Application Data

(63) Continuation-in-part of application No. 10/256,493, filed on Sep. 26, 2002, which is a continuation-in-part of application No. 10/007,204, filed on Nov. 8, 2001, now Pat. No. 6,863,680.

(51) Int. Cl.
*A61B 17/08* (2006.01)
*A61M 31/00* (2006.01)

(52) U.S. Cl. .................................. 606/213; 604/60
(58) Field of Classification Search ................ 606/213, 606/215, 216, 228–231; 604/11, 13, 15, 604/60, 131
See application file for complete search history.

(56) References Cited

U.S. PATENT DOCUMENTS

| | | |
|---|---|---|
| 581,235 A | 4/1897 | Kenyon |
| 1,578,517 A | 3/1926 | Hein |
| 2,086,580 A | 7/1937 | Shirley |
| 2,370,319 A | 2/1945 | Lippincott |
| 2,465,357 A | 3/1949 | Correll |
| 2,492,458 A | 12/1949 | Bering, Jr. |
| 2,507,244 A | 5/1950 | Correll |
| 2,558,395 A | 6/1951 | Studer |
| 2,597,011 A | 5/1952 | MacMasters et al. |
| 2,680,442 A | 6/1954 | Linzmayer |

(Continued)

FOREIGN PATENT DOCUMENTS

| | | |
|---|---|---|
| EP | 0032826 | 7/1981 |

(Continued)

OTHER PUBLICATIONS

Allison, D., et al., "Percutaneous Liver Biopsy and Track Embolization With Steel Coils," *Radiology*, (1988) pp. 261-263, vol. 169, No. 1.

(Continued)

*Primary Examiner*—Sharon Kennedy
(74) *Attorney, Agent, or Firm*—Miller, Matthias & Hull

(57) ABSTRACT

A system for delivering hemostasis promoting material of the present invention allows the hemostasis promoting material to be delivered to a blood vessel puncture site by fluid pressure. The system allows the hemostasis promoting material to be delivered through an introducer sheath which is already in place within a tissue tract. This system includes a control tip which is insertable through the introducer sheath to locate and occlude the blood vessel puncture site and a hydration chamber for receiving and delivering the hemostasis promoting material to the blood vessel puncture site. The system accurately locates the blood vessel wall at a puncture site and for properly placing a hemostasis plug over the puncture site.

11 Claims, 19 Drawing Sheets

U.S. PATENT DOCUMENTS

| | | |
|---|---|---|
| 2,761,446 A | 9/1956 | Reed |
| 2,814,294 A | 11/1957 | Figge |
| 2,824,092 A | 2/1958 | Thompson |
| 2,874,776 A | 2/1959 | Hooe |
| 2,899,362 A | 8/1959 | Sieger, Jr. et al. |
| 3,157,524 A | 11/1964 | Artandi |
| 3,358,689 A | 12/1967 | Higgins |
| 3,411,505 A | 11/1968 | Nobis |
| 3,724,465 A | 4/1973 | Duchane |
| 3,736,939 A | 6/1973 | Taylor |
| 4,000,741 A | 1/1977 | Binard et al. |
| 4,098,728 A | 7/1978 | Rosenblatt |
| 4,211,323 A | 7/1980 | Olsen |
| 4,218,155 A | 8/1980 | Weidner |
| 4,219,026 A | 8/1980 | Layton |
| 4,224,945 A | 9/1980 | Cohen |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zuloowski |
| 4,404,970 A | 9/1983 | Sawyer |
| 4,405,314 A | 9/1983 | Copi |
| 4,515,637 A | 5/1985 | Cioca |
| 4,573,576 A | 3/1986 | Krol |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,644,649 A | 2/1987 | Seaman et al. |
| 4,645,488 A | 2/1987 | Matukas |
| 4,699,616 A | 10/1987 | Norwak |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,832,688 A | 5/1989 | Sagae et al. |
| 4,836,204 A | 6/1989 | Landymore et al. |
| 4,839,204 A | 6/1989 | Yoshino |
| 4,850,960 A | 7/1989 | Grayzel |
| 4,852,568 A | 8/1989 | Kensey |
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofaky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,049,138 A | 9/1991 | Chevalier et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,129,889 A | 7/1992 | Hahn |
| 5,163,904 A | 11/1992 | Lampropoulos et al. |
| 5,167,624 A | 12/1992 | Butler et al. |
| 5,192,290 A | 3/1993 | Hilgal |
| 5,192,300 A | 3/1993 | Fowler |
| 5,192,301 A | 3/1993 | Kamiya et al. |
| 5,195,988 A | 3/1993 | Haaga |
| 5,219,899 A | 6/1993 | Panster et al. |
| 5,220,926 A | 6/1993 | Jones |
| 5,221,259 A | 6/1993 | Weldon et al. |
| 5,232,453 A | 8/1993 | Plass et al. |
| 5,242,683 A | 9/1993 | Klaveness |
| 5,254,105 A | 10/1993 | Haaga |
| 5,275,616 A | 1/1994 | Fowler |
| 5,282,827 A | 2/1994 | Kensey et al. |
| 5,310,407 A | 5/1994 | Casale |
| 5,320,639 A | 6/1994 | Rudnick |
| 5,322,515 A | 6/1994 | Karas et al. |
| 5,325,857 A | 7/1994 | Nabai et al. |
| 5,334,216 A | 8/1994 | Vidal et al. |
| 5,342,388 A | 8/1994 | Toller |
| 5,350,399 A | 9/1994 | Erlebacher et al. |
| 5,352,211 A | 10/1994 | Merskelly |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammersiag |
| 5,385,550 A | 1/1995 | Su et al. |
| 5,388,588 A | 2/1995 | Nabai et al. |
| 5,391,183 A | 2/1995 | Janzen et al. |
| 5,399,361 A | 3/1995 | Song et al. |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,443,481 A | 8/1995 | Lee |
| 5,447,502 A | 9/1995 | Haaga |
| 5,458,570 A | 10/1995 | May, Jr. |
| 5,462,194 A | 10/1995 | Barawell |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers |
| 5,490,736 A | 2/1996 | Haber |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammershiag |
| 5,540,715 A | 7/1996 | Katseros et al. |
| 5,542,914 A | 8/1996 | Van Iten |
| 5,545,175 A | 8/1996 | Abidin et al. |
| 5,545,178 A | 8/1996 | Kensey et al. |
| 5,558,853 A | 9/1996 | Quay |
| 5,571,168 A | 11/1996 | Toro |
| 5,591,204 A | 1/1997 | Janzen et al. |
| 5,591,205 A | 1/1997 | Fowler |
| 5,601,601 A | 2/1997 | Tal et al. |
| 5,601,602 A | 2/1997 | Fowler |
| 5,601,603 A | 2/1997 | Illi |
| 5,620,461 A | 4/1997 | Muijs Van De Moer |
| 5,645,566 A | 7/1997 | Brennenman et al. |
| 5,649,547 A | 7/1997 | Ritchart et al. |
| 5,653,730 A | 8/1997 | Hammersiag |
| 5,665,107 A | 9/1997 | Hammersiag |
| 5,674,346 A | 10/1997 | Kundel |
| 5,676,689 A | 10/1997 | Kensey |
| 5,681,279 A | 10/1997 | Roper et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,931,165 A | 8/1999 | Reich et al. |
| 5,984,950 A | 11/1999 | Cragg et al. |
| 6,007,563 A | 12/1999 | Nash et al. |
| 6,027,471 A | 2/2000 | Fallon et al. |
| 6,027,482 A | 2/2000 | Imbert |
| 6,033,427 A | 3/2000 | Lee |
| 6,056,768 A | 5/2000 | Cates et al. |

| | | | |
|---|---|---|---|
| 6,066,325 A | 5/2000 | Wallace et al. | |
| 6,071,300 A | 6/2000 | Brenneman et al. | |
| 6,071,301 A | 6/2000 | Cragg et al. | |
| 6,086,607 A | 7/2000 | Cragg et al. | |
| 6,090,130 A | 7/2000 | Nash et al. | |
| 6,126,675 A | 10/2000 | Shchervinsky et al. | |
| 6,161,034 A | 12/2000 | Burbank et al. | |
| 6,162,192 A | 12/2000 | Cragg et al. | |
| 6,183,497 B1 | 2/2001 | Sing et al. | |
| 6,200,328 B1 | 3/2001 | Cragg et al. | |
| 6,315,753 B1 | 11/2001 | Cragg | |
| 6,371,974 B1 | 4/2002 | Brenneman et al. | |
| 6,440,151 B1 | 8/2002 | Cragg et al. | |
| 6,440,153 B1 | 8/2002 | Cragg et al. | |
| 6,447,534 B1 | 9/2002 | Cragg et al. | |
| 6,503,222 B1 | 1/2003 | Lo | |
| 6,527,734 B1 | 3/2003 | Cragg et al. | |
| 6,540,735 B1 | 4/2003 | Ashby et al. | |
| 6,544,236 B1 | 4/2003 | Cragg et al. | |
| 6,610,026 B1 | 8/2003 | Cragg et al. | |
| 2002/0002889 A1 | 1/2002 | Ashby et al. | |
| 2002/0016612 A1 | 2/2002 | Ashby et al. | |
| 2002/0038133 A1 | 3/2002 | Sing et al. | |
| 2002/0042378 A1 | 4/2002 | Reich et al. | |
| 2002/0062104 A1 | 5/2002 | Ashby et al. | |
| 2002/0156495 A1 | 10/2002 | Brenneman et al. | |
| 2003/0028140 A1 | 2/2003 | Greff et al. | |
| 2003/0088269 A1 | 5/2003 | Ashby | |
| 2003/0088271 A1 | 5/2003 | Cragg et al. | |
| 2003/0120258 A1 | 6/2003 | Ashby et al. | |
| 2003/0135237 A1 | 7/2003 | Cragg et al. | |
| 2004/0019328 A1 | 1/2004 | Sing et al. | |
| 2004/0019330 A1 | 1/2004 | Ashby | |

FOREIGN PATENT DOCUMENTS

| | | |
|---|---|---|
| EP | 0476178 | 3/1992 |
| EP | 0482350 | 4/1992 |
| EP | 0557963 | 2/1993 |
| EP | 0637431 | 11/1994 |
| EP | 0637432 B1 | 10/1997 |
| FR | 2641692 | 7/1990 |
| GB | 1509023 | 4/1978 |
| GB | 1569660 | 6/1980 |
| SU | 782814 | 11/1980 |
| SU | 1088709 A | 4/1984 |
| WO | WO 91/12847 | 9/1991 |
| WO | WO 94/02072 | 2/1994 |
| WO | WO 94/28800 | 12/1994 |
| WO | WO 95/28124 | 10/1995 |
| WO | WO 95/32669 | 12/1995 |
| WO | WO 95/32671 | 12/1995 |
| WO | WO 95/32679 | 12/1995 |
| WO | WO 96/08208 | 3/1996 |
| WO | WO 96/24290 | 8/1996 |
| WO | WO 97/07934 | 3/1997 |
| WO | WO 97/09934 | 3/1997 |
| WO | WO 98/06346 | 2/1998 |
| WO | WO 99/66834 | 12/1999 |

OTHER PUBLICATIONS

Berman, Howard L., et al., "Guided Direct Antegrade Puncture of the Superficial Femoral Artry;" *AJR*, (Sep. 1986) pp. 632-634, American Roentgen Ray Society, vol. 147, Valhalla, NY.

Berman, Howard L., et al "Modification of the Cope Drainage Catheter to Facilitate Placement" *AJR* (Jan. 1986) pp. 169-170; American Roentgen Ray Society, vol. 146, Valhalla, NY.

J. Bryne, "Review Article: Endovascular Treatments For Intracranial Aneurysms," *The British Journal of Radiology* (Oct. 1996) pp. 891-899, vol. 69, No. 826.

Chuang, V., et al., "Sheath Needle For Liver Biopsy In High-Risk Patience," *Radiology*, (1988) pp. 261-262, vol. 166.

Correll, John T. et al., "Certain Properties of a New Physiologically Absorbable Sponge," pp. 233-235.

Correll, John T. et al., "Biologic Investigations Of a New Absorbable Sponge," *Surgery, Gynecology and Obstetrics*, pp. 585-589.

Di Seni, Ricardo, et al, "Part 1, Embolotherapy: Agents, Equipment, and Techniques," Vascular Embolotherapy, vol. 4, pp. 29 & 33.

Fandrich, C., et al. "Small Gauge Gelfoam Plug Liver Biopsy In High Risk Patients", *Australian Radiology*, vol. 40, pp. 230-234 (1996).

Foran, J., et al. "Early Mobilisition After Percutaneous Cardiac Catheterisations Using Collagen Plug (VasoSeal) Haemostasis," Br Heart J, vol. 69, pp. 424-429 (1993).

Gibbs, J., "Femoral Arterial Hemostasis Using a Collagen Plug After Coronary Artery Stent Implantation," *Journal Interventional Cardiology*, vol. 5, No. 2, pp. 85-88 (1992).

*Journal Of Interventional Cardiology*, vol. 5 No. 2, Jun. 1992, Futura Publishing Company, Inc,.

Kassell, Neal F., et al. "Size of Intracranial Aneurysm," *Neurosurgery*, vol. 12, No. 3, pp. 291-297, (1983).

Kiemeneij, Ferdinand, et al., "Improved Anticoagulation Management After Palmaz Schatz Coronary Stent Implantation by Sealing the Arterial Puncture Site With a Vascular Hemostasis Device", vol. 30, pp. 317-322 (1993).

Kussmaul, W.G., et al, "Rapid Arterial Hemostasis and Decreased Access Site Complications After Cardiac Catheterization and Angioplasty: Results of a Randomized Trial of a Novel Hemostatic Device", J. Am. Coll. Card., vol. 25, pp. 1685-1692 (1995).

Pharmacia & Upjohn manufacturer brochure gelfoam sterile sponge, sterile powder and sterile film, pp. 1-34 (May 1997).

Pharmacia & Upjohn manufacturer brochure gelfoam sterile powder, (Feb. 1996).

Pharmacia & Upjohn manufacturer brochure, "gelfoam sterile powder" (Mar. 1996).

Pharmacia & Upjohn manufacturer brochure (Sep. 1996).

Pharmacia & Upjohn manufacturer specification, "Gelfoam sterile sponge, sterile powder and sterile film" pp. 1-23 (Nov. 1996).

Riley, S. A., et al, "Percutaneous Liver Biopsy With Plugging Of Needle Track: A Safe Method For Use In Patients With Impaired Coagulation," *The Lancet*, p. 436 (1964).

Saddekni, Sovhell, et al "Antegrade Catheterization of the Superficial Femoral Artery," *Radiology*, vol. 157, No. 2, pp. 531-532 (Nov. 1985).

Sanborn, T., et al., "Multicenter Randomized Trial Comparing A Percutaneous Collagen Hemostasis Device With Conventional Manual Compression After Diagnostic Angiograpgy And Angioplasty," J. Am. Coll. Card., vol. 22, No. 5 pp. 1273-1279 (Nov. 1, 1993).

Scharader, R., et al., "Collagen Application for Sealing of Arterial Puncture Sites in Comparison to Pressure Dressing: A Randomized Trial", Catheterization & Cardiovascular Diagnosis (1992) pp. 298-302.

Schievink, Wouter I., "Review Articles: Medical Progress," *The New England Journal of Medicine*; vol. 336, No. 1, pp. 28-40, Jan. 2, 1997.

Silber, S., et al, "Rapid Hemostasis Of Arterial Puncture Sites with Collagen in Patients Undergoing Diagnostic Interventional Cardiac Catheterization", *Clinical Cardiology*, vol. 20, pp. 981-992, (Dec. 1997).

Smith, T., et al, "Percutaneous Transhepatic Liver Biopsy with Tract Embolization", Radiology, vol. 198, pp. 769-774 (1996).

Szikora, et al. "Combined Use of Stents and Coils to Treat Experimental Wide-Necked Carotid Aneurysms: Preliminary Results," *Am J Neuroradiol*; vol. 15, pp. 1091-1102, Jun. 1994.

Szikora, et al. "Endovascular Treatment of Experimental Aneurysms with Liquid Polymers: The Provective Potential Of Stents," *Neurosurgery*, vol. 38, No. 2, Feb. 1996, pp. 339-347.

Turjman, F., et al., "Combined Stent Implantation and Endosaccular Coil Placement for Treatment of Experimental Wide-Necked Aneurysms: A Feasibility Study in Swine," *Am J. Neuroradiol*, vol. 15, pp. 1087-1090, Jun. 1994.

Vogelzang, Robert L., "A Modified Cope Introducing Dilator to Allow Straight Guide Wire Introduction," AJR, vol. 146 pp. 381-382 (Feb. 1986).

Yoshimoto, et al, "Cerebral Aneurysms Unrelated To Arterial Bifurcations," *Acta Neurochir* (Wien) vol. 138, pp. 958-964 (1996).

Zins, M., et al., "US-guided Percutaneous Liver Biopsy with Plugging of the Needle Track: A Prospective Study in 72 High-Risk Patients" Radiology, vol. 184, pp. 841-843 (Sep. 1992).

(125) Ashby, Mark et al; U.S. Appl. No. 10/287,922; filed: Nov. 4, 2002; entitled: Apparatus And Method For Inhibiting Blood Loss.

(130) Ashby, Mark et al; U.S. Appl. No. 10/069,107; filed: Dec. 16, 2002; entitled: Device And Method For Determining A Depth Of An Incision.

(144) Ashby, Mark et al; U.S. Appl. No. 10/278,710; filed: Oct. 22, 2002; entitled: System and Method for Facilitating Hemostasis of Blood Vessel Punctures With Absorbable Sponge.

(152) Ashby, Mark et al; U.S. Appl. No. 10/334,770; filed: Dec. 31, 2002; entitled: Improved System and Method for Facilitating Hemostasis with Absorbable Sponge.

(154) Ashby, Mark et al; U.S. Appl. No. 10/421,680; filed Apr. 22, 2003; entitled: Puncture Closure System With Pin And Pull Technique.

(159) Ashby, Mark et al; U.S. Appl. No. 10/462,065; filed: Jun. 12, 2003; entitled: Enhanced Bleed Back System.

(160) Ashby, Mark et al, U.S. Appl. No. 10/462,064; filed: Jun. 12, 2003; entitled: Release Mechanism.

(161) Ashby, Mark et al; U.S. Appl. No. 10/461,587; filed: Jun. 12, 2003: Dissolvable Closure Device.

(162) Ashby, Mark et al; U.S. Appl. No. 10/461,035; filed: Jun. 13, 2003; entitled: System And Method For Delivering Hemostasis Promoting Material To A Blood Vessel Puncture Site Using a Cannula.

(163) Ashby, Mark et al; U.S. Appl. No. 10/461,006; filed: Jun. 13, 2003; entitled: System and Method for Delivering Hemostasis Promoting Material to a Blood Vessel Puncture with a Staging Tube.

(164) Ashby, Mark et al; U.S. Appl. No. 10/460,859; filed: Jun. 12, 2003; entitled: Hemostatic Device Including a Capsule.

Ashby, Mark et al; U.S. Appl. No. 10/754,824; filed: Jan. 9, 2004; entitled: Sheath-Mounted Arterial Plug Delivery Device.

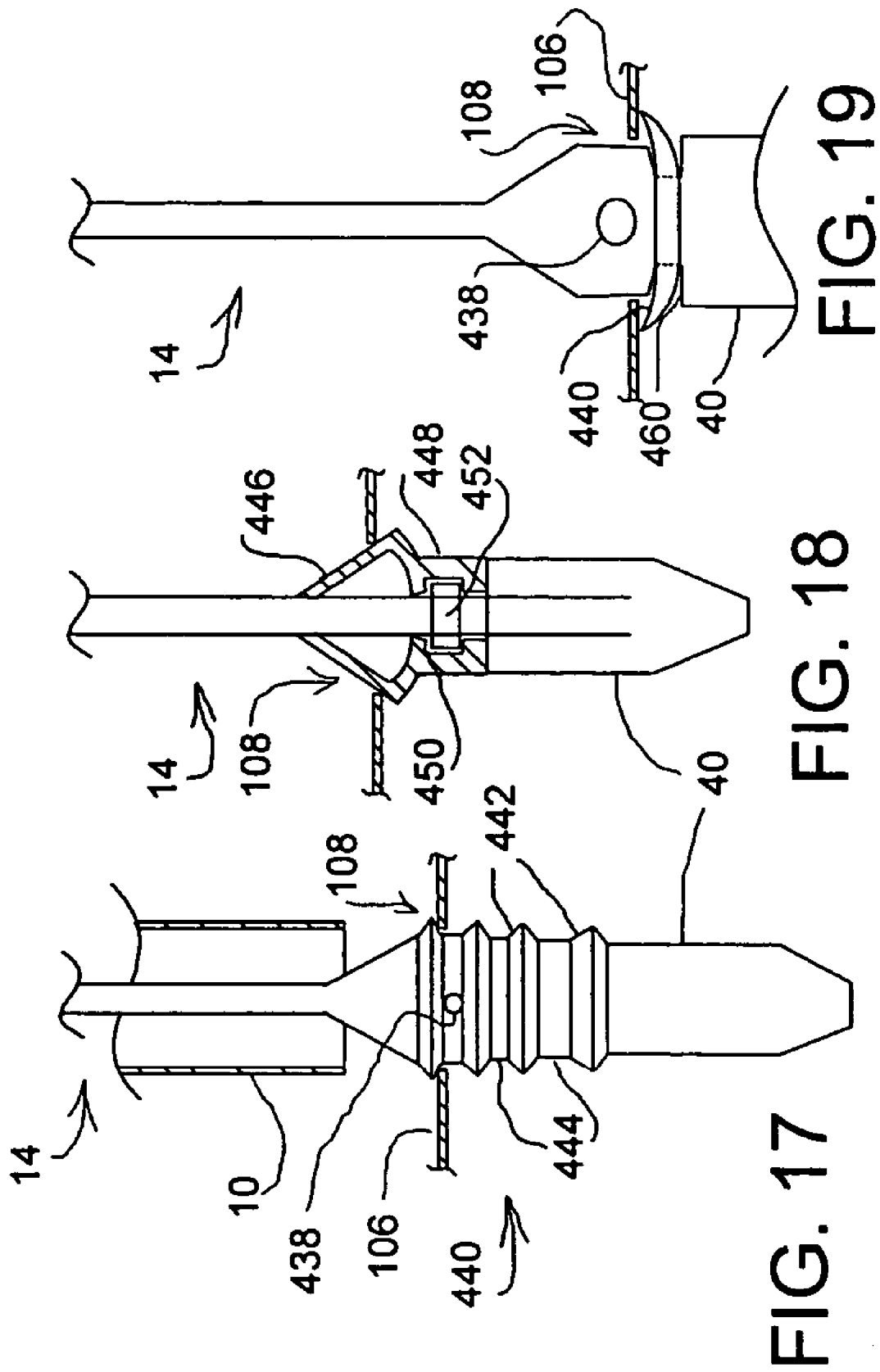

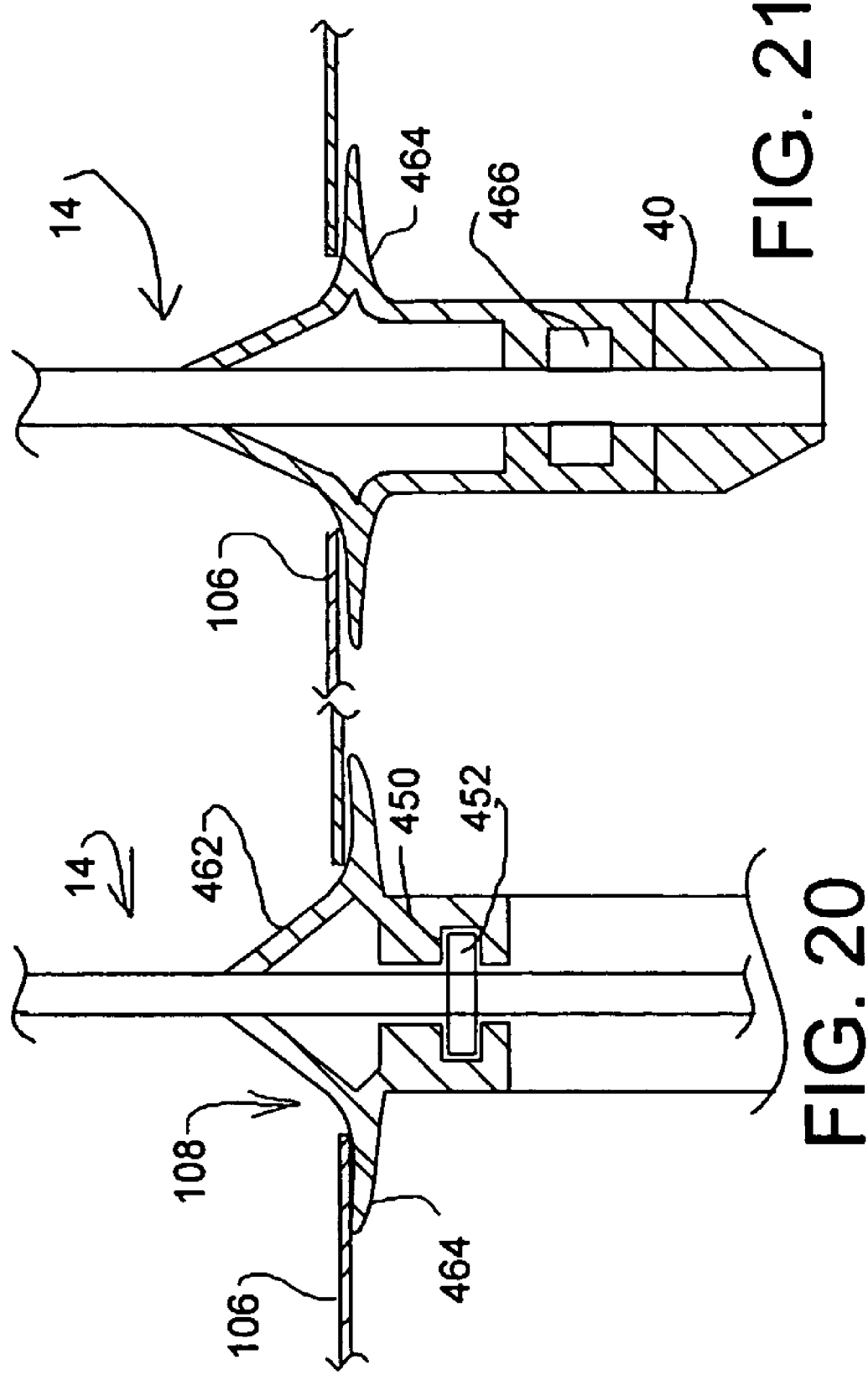

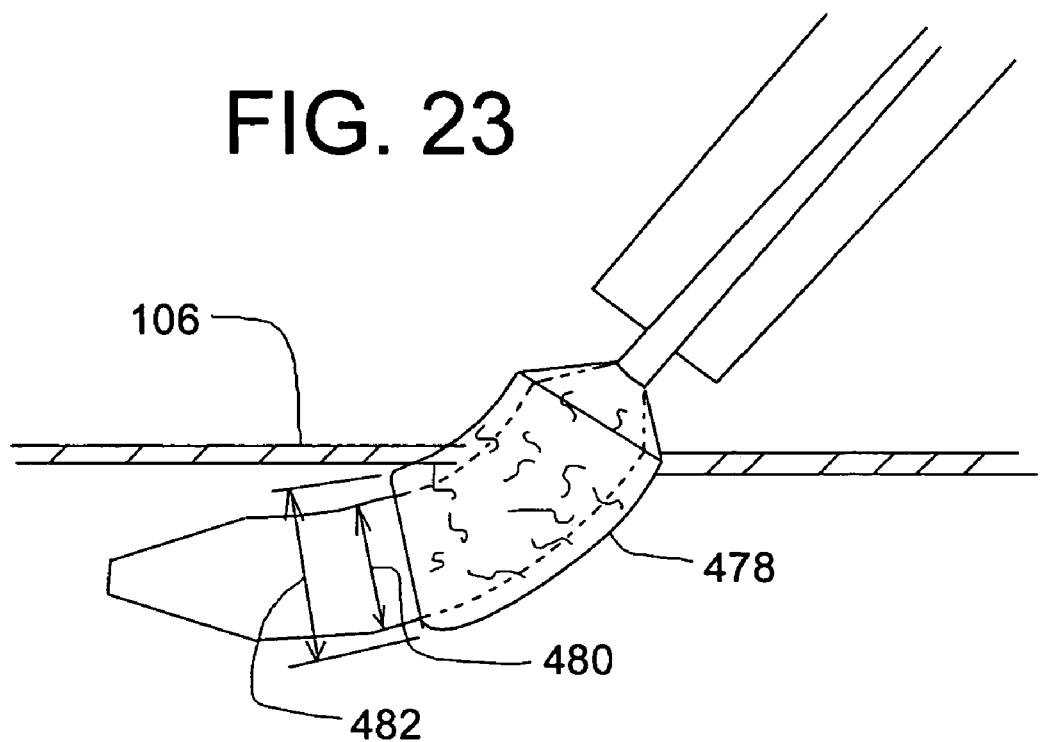
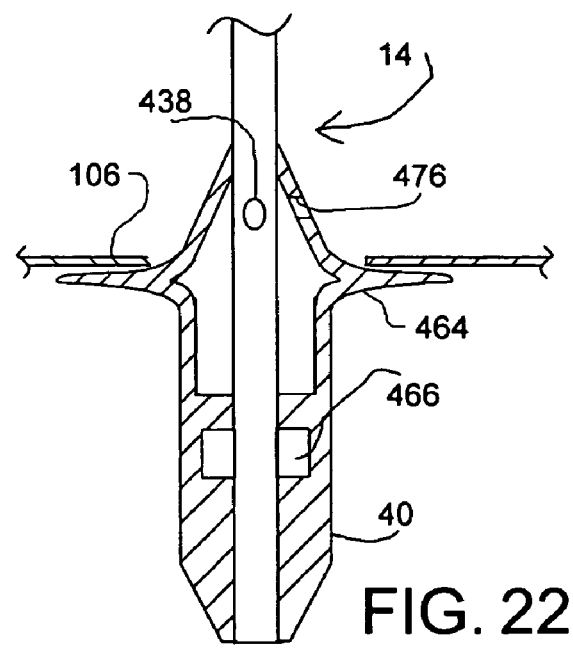

PLEDGET-HANDLING SYSTEM AND METHOD FOR DELIVERING HEMOSTASIS PROMOTING MATERIAL TO A BLOOD VESSEL PUNCTURE SITE BY FLUID PRESSURE

RELATED PATENT APPLICATIONS

This application is a continuation in part of the following prior U.S. patent applications 1) Ser. No. 10/256,493 filed Sep. 26, 2002 and titled SYSTEM AND METHOD FOR DELIVERING HEMOSTASIS PROMOTING MATERIAL TO A BLOOD VESSEL PUNCTURE SITE BY FLUID PRESSURE and 2) Ser. No. 10/007,204 filed Nov. 8, 2001 now U.S. Pat. No. 6,863,680 and titled SYSTEM AND METHOD FOR DELIVERING HEMOSTASIS PROMOTING MATERIAL TO A BLOOD VESSEL PUNCTURE SITE BY FLUID PRESSURE.

FIELD OF THE INVENTION

The invention relates to a system and method for delivering hemostasis promoting material to a blood vessel puncture site by fluid pressure, and more particularly, the invention relates to an improved system and method for delivery of absorbable sponge material for sealing of a blood vessel puncture site.

DESCRIPTION OF THE RELATED ART

A large number of diagnostic and interventional procedurals involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

A system which addresses many of these problems is described in U.S. Pat. No. 6,162,192 which delivers a hydrated pledget of absorbable sponge material to a location outside the blood vessel to facilitate hemostasis. However, this system involves the removal of the introducer sheath used during the intravascular procedure and the insertion of a dilator and introducer into the tissue tract vacated by the introducer sheath to place the absorbable sponge. It would be desirable to reduce the number of steps involved in delivery of a hemostasis promoting material by allowing the material to be delivered through an introducer sheath already in place within the tissue tract and used in the intravascular procedure.

Accordingly, it would be desirable to provide a system for accurately locating the blood vessel wall at a puncture site and for properly placing a hemostasis plug over the puncture site where the locating and placing steps are performed through the introducer sheath already in place in the blood vessel.

SUMMARY OF THE INVENTION

The present invention relates to a system for delivering hemostasis promoting material to a blood vessel puncture site through a sheath already in place in the blood vessel.

In accordance with one aspect of the invention, a pledget handling system is provided. The pledget handling system facilitates consistent hydration of the pledget, provides for effective staging of the pledget, and prevents early pledget delivery.

In accordance with another aspect of the invention, a system for delivering hemostasis promoting material includes an introducer sheath, a control tip coupled to the introducer sheath; and, seal means disposed around a portion of said control tip to prevent blood from passing into and through the introducer sheath. The seal means also protects against unwanted transmission of materials from the sheath into the blood vessel.

BRIEF DESCRIPTION OF THE DRAWING FIGURES

The invention will now be described in greater detail with reference to the preferred embodiments illustrated in the accompanying drawings, in which like elements bear like reference numerals, and wherein:

FIG. 17 is an alternative embodiment for delivering hemostasis promoting material including an introducer sheath, a control tip coupled to and extending from the introducer sheath; and, seal means disposed around a portion of said control tip.

FIG. 18 is an alternative embodiment.

FIG. 19 is an alternative embodiment.

FIG. 20 is an alternative embodiment.

FIG. 21 is an alternative embodiment.

FIG. 22 is an alternative embodiment.

FIG. 23 is an alternative embodiment.

DETAILED DESCRIPTION OF THE PREFERRED EMBODIMENTS

A system for delivering hemostasis promoting material of the present invention allows the hemostasis promoting material to be delivered to a blood vessel puncture site by fluid pressure. The system allows the hemostasis promoting material to be delivered through an introducer sheath which is already in place within a tissue tract. This system includes a control tip which is insertable through the introducer sheath to locate and occlude the blood vessel puncture site and a hydration chamber for receiving and delivering the hemostasis promoting material to the blood vessel puncture site.

Although the present invention is particularly designed for delivering a hemostasis promoting material in the form of an absorbable sponge through the introducer sheath by fluid pressure, it should be understood that the system may also be used for delivering other hemostasis promoting materials which are useful for sealing a puncture site. The use of an absorbable hydrated sponge material allows the delivery of more absorbable sponge material down through a smaller sheath by allowing the sponge material to be hydrated and compressed. Once delivered, the absorbable sponge rapidly expands to fill the entire width of the tissue tract and provides hemostasis at the puncture site.

In the context of the present invention, "pledget" means a piece of sponge formed into a generally elongated shape having a size which allows delivery in a hydrated state through an introducer sheath, delivery cannula or introducer to a site of a puncture in a blood vessel.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which, when implanted within a human or other mammalian body, is absorbed or resorbed by the body.

"Hydrate" means to partially or fully saturate with a fluid, such as saline, water, blood contrast agent, thrombin, ionic solutions, therapeutic agents, or the like.

Figure 1:
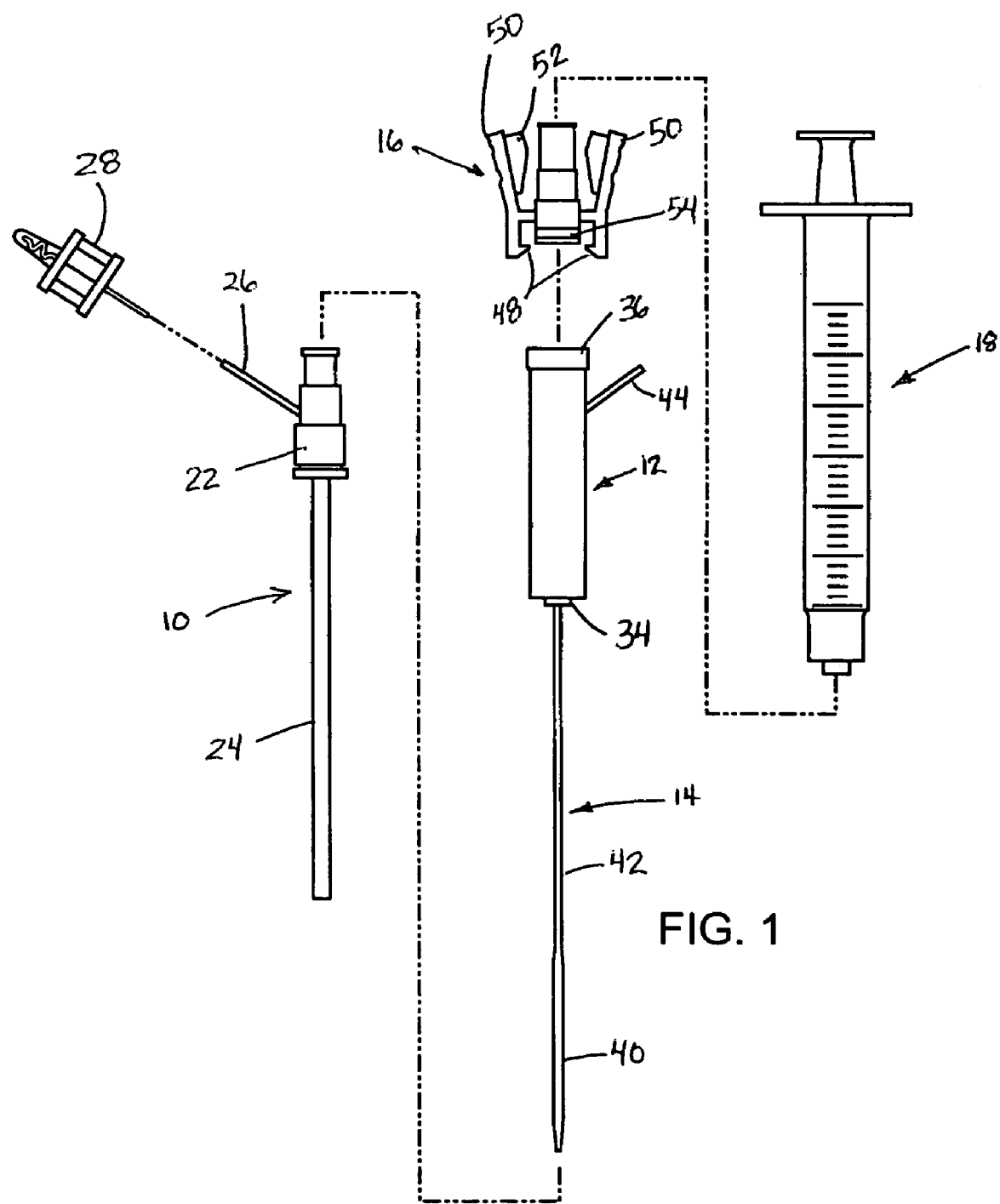
FIG. 1 is an exploded side view of a first embodiment of a system for delivering hemostasis promoting material to a blood vessel puncture site by fluid pressure.

The system of FIG. 1 includes an introducer sheath 10, a hydration chamber 12 with an attached control tip 14, a coupler 16, and a syringe 18. The introducer sheath 10 is an intravascular access sheath as is conventionally used for procedures such as coronary angioplasty and stenting procedures. The introducer sheath 10 includes a proximal hub 22 connected to a tubular sheath 24. A vent tube 26 is in fluid communication with an interior of the hub 22 for purposes of providing a visual bleed back indication which will be discussed in further detail below. In the embodiment illustrated in FIG. 1, a vent cap 28 is provided for opening and closing the vent tube 26 manually.

The hydration chamber 12 is configured to receive a pledget of absorbable sponge material for hydration of the pledget and delivery of the pledget through the introducer sheath 10. A proximal end of the hydration chamber 12 includes a flange 36 or other connecting element for receiving the coupler 16; A distal end 34 of the hydration chamber 12 connects to the proximal hub 22 of the introducer sheath 12. The control tip 14 has an enlarged distal end 40 configured to be received in the puncture in the blood vessel and to control blood flow through the puncture in the blood vessel. The enlarged distal end 40 is connected to a smaller diameter control tip tube 42 which extends from the enlarged distal end through the distal end of the hydration chamber 12 and out a side of the hydration chamber 12 to a proximal end 44 of the control tip. The enlarged distal end 40 of the control tip performs the multiple functions of controlling blood flow through the blood vessel puncture, providing an indication of the position of the distal end of the introducer sheath, and guiding the hemostasis promoting material delivery system over a guidewire.

The coupler 16 allows the syringe 18 to be connected to the hydration chamber 12. Removal of the coupler 16 from the hydration chamber 12 allows the pledget of absorbable sponge material to be easily inserted into the hydration chamber in its dry form. Upon connection of the coupler 16 to the hydration chamber 12 the conventional syringe 18 will be connected to the coupler 16 for injection of fluid into the hydration chamber. The coupler 16 includes a seal 54 and two or more locking tabs 48 which lock over the flange 36 of the hydration chamber and are releasable by pressing on two wings 50 of the coupler. Stops 52 on the interior surfaces of the wings 50 prevent the coupler 16 from being removed from the hydration chamber 12 when a syringe 18 is mounted on the coupler. It should be understood that many other coupler designs may also be used without departing from the present invention.

Figure 2:
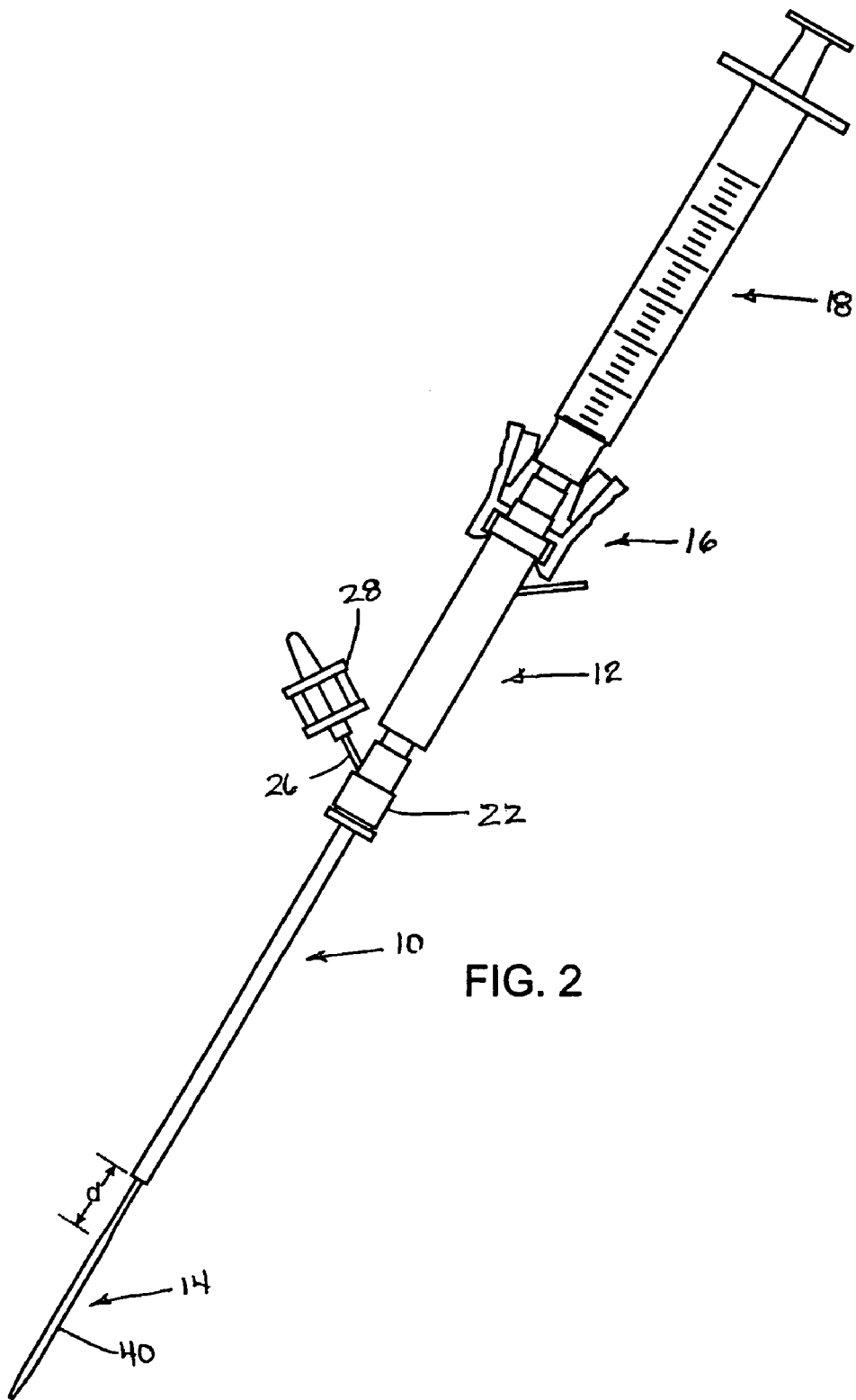
FIG. 2 is an assembled side view of the system of FIG. 1.
Figure 3:
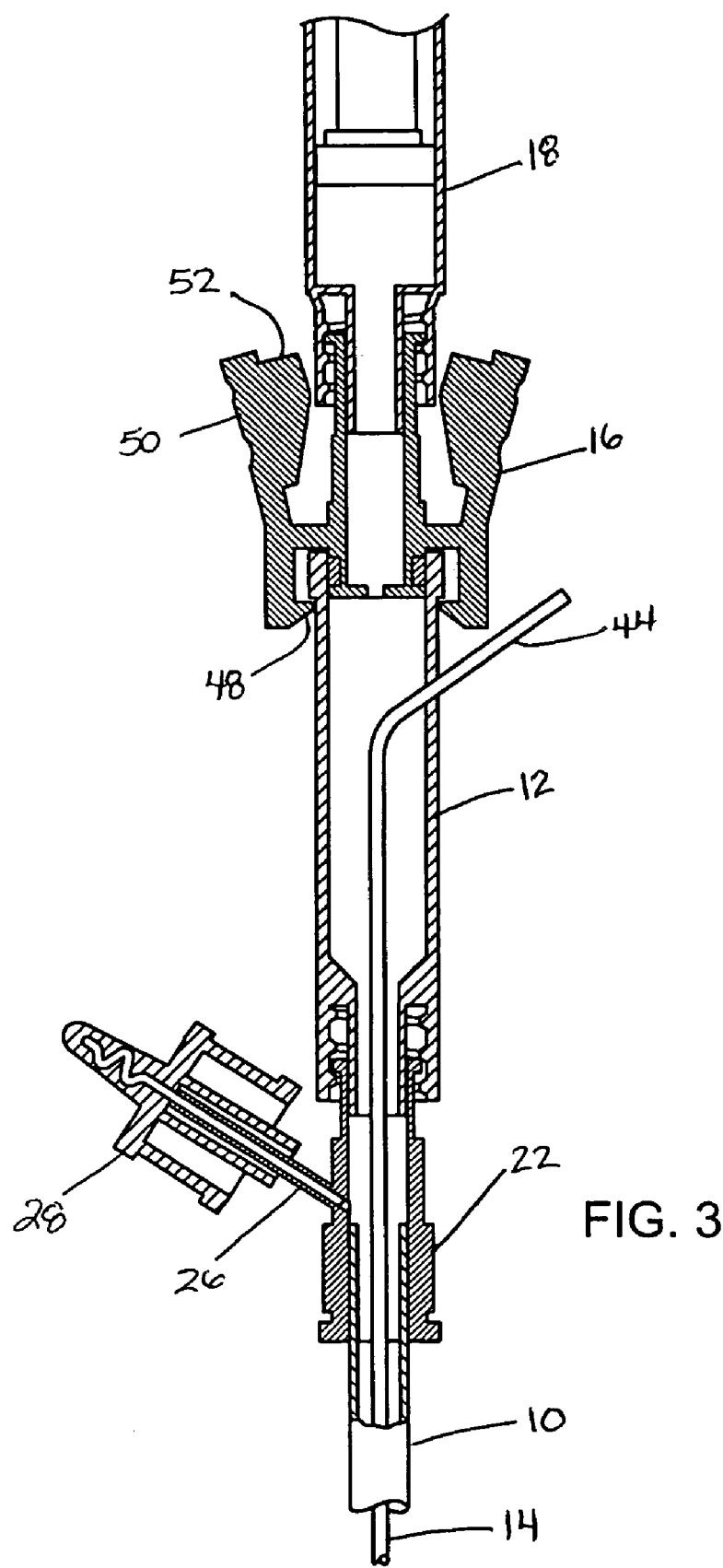
FIG. 3 is a side cross sectional view of a portion of the system of FIG. 2.
Figure 4:
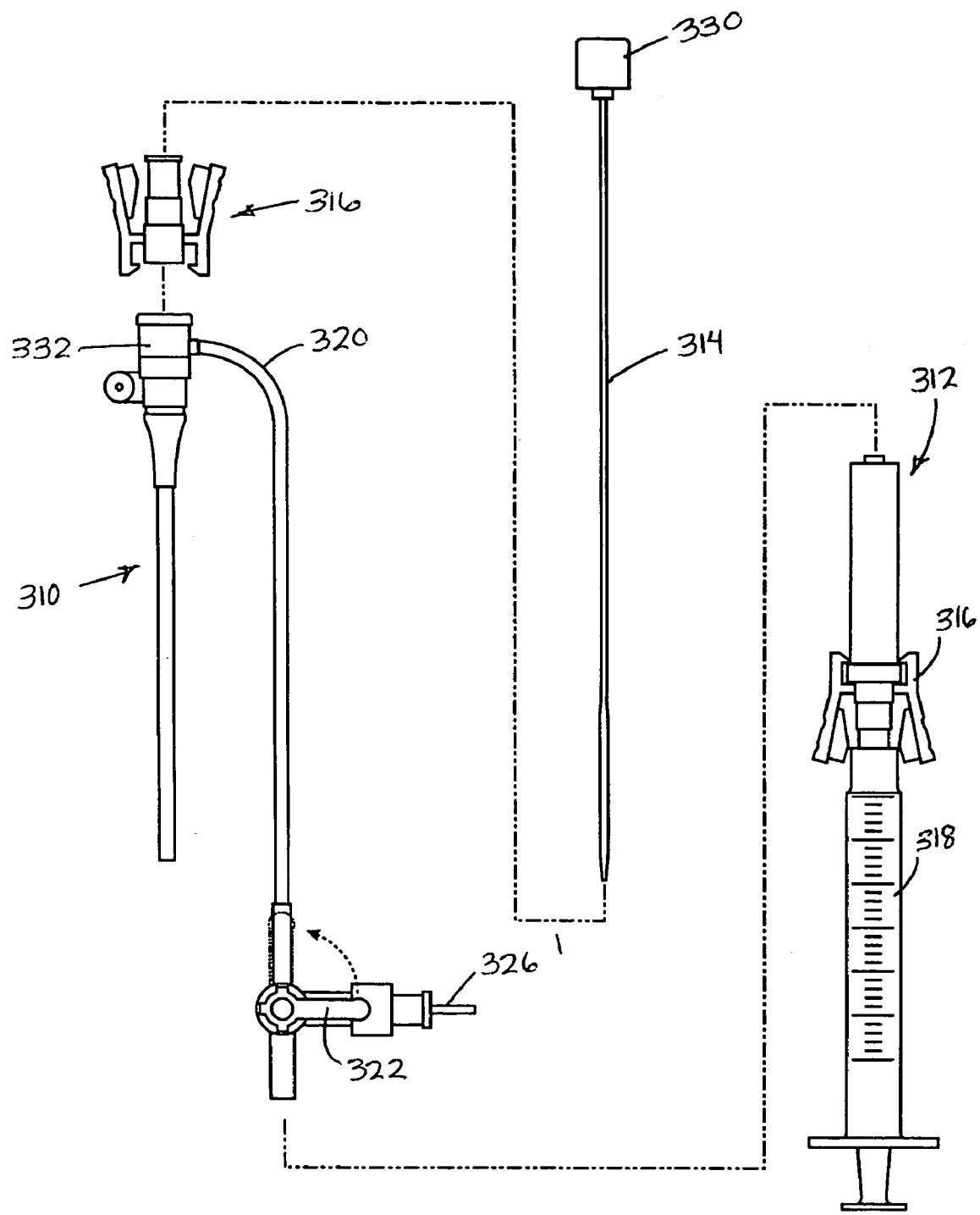
FIG. 4 is an exploded side view of a further system for delivering hemostasis promoting material to a blood vessel puncture site by fluid pressure with the material delivered to a side branch of the sheath.
Figure 5:
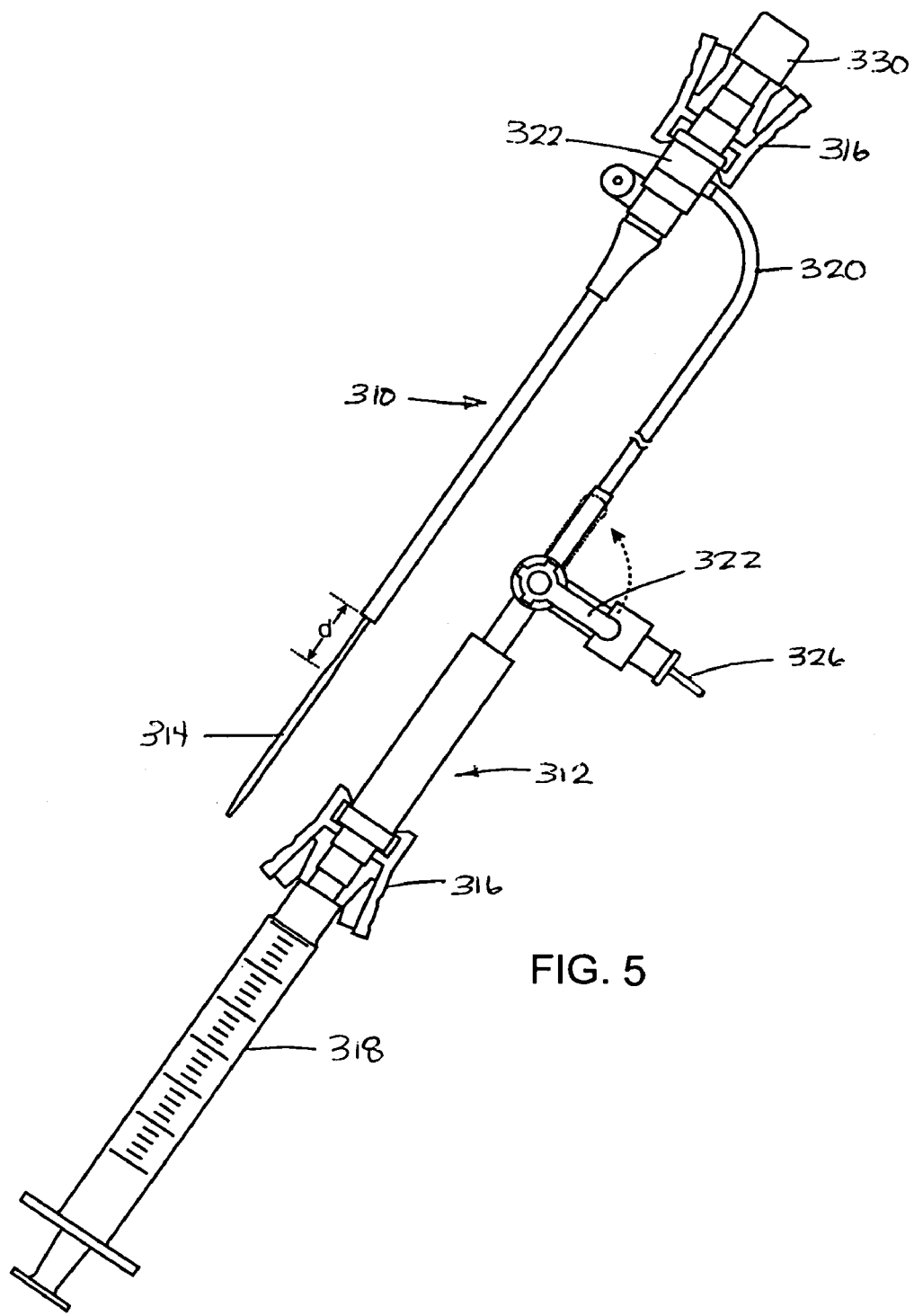
FIG. 5 is an assembled side view of the system of FIG. 4.

In use, the system of FIGS. 1, 2, and 3 is assembled with a sponge placed inside the hydration chamber 12 and a syringe 18 containing water, saline solution, or other fluid attached to the hydration chamber by the coupler 16. The sponge is hydrated and staged or moved, to a position at the distal end of the hydration chamber as will be described in further detail below. The syringe 18 is preferably capable of generating a high pressure with a relatively low plunger force such as a 1 cc syringe.

The introducer sheath 10 is placed in the blood vessel puncture of a patient in a conventional manner for performance of the intravascular procedure. After the intravascular procedure, the introducer sheath 10 and a guidewire (not shown) are maintained in place extending into the blood vessel. The control tip 14 is threaded over the proximal end of the guidewire and the hydration chamber 12 and control tip 14 are advanced into the introducer sheath until the hydration chamber distal end 34 is engaged with the hub 22 of the introducer sheath 10. Bleed back is observed by a variety of methods which will be described below with respect to FIG. 3. In the embodiment of FIG. 3, the vent cap 28 is removed from the vent tube 26 to observe bleed back. The introducer sheath 10, hydration chamber 12, and control tip 14, are withdrawn together slowly from the puncture site until the bleed back observed from the vent tube 26 stops. The bleed back stops when the enlarged distal end 40 of the control tip 44 is positioned in the blood vessel puncture preventing blood from escaping from the puncture. The distance d between the distal end of the tubular sheath 24 and the enlarged distal end 40 of the control tip 14 is selected so that the point at which bleed back stops indicates that the distal end of the introducer sheath 10 is located at a desired delivery location for delivery of the hemostasis promoting material to the blood vessel puncture site. The distance d will be selected to correspond to the size of the pledget to be delivered to the puncture site and will be selected such that the hemostasis promoting material is located in the tissue tract adjacent the blood vessel without extending into the lumen of the blood vessel.

FIG. 3 illustrates a vent tube 26 with a vent cap 28 for observing bleed back. When the vent cap 28 is removed from the vent tube 26 blood is able to pass from the distal end of the introducer sheath 10 through the introducer sheath and out of the vent tube. The vent tube 26 has a relatively small diameter which is selected to provide a very noticeable spurt or stream of blood to indicate bleed back has occurred. In contract, the observance of bleed back from a larger tube such as the introducer sheath would result in an oozing or dripping bleed back indication which is difficult for the user to use as a precise indicator of position. According to one preferred embodiment, the vent tube 26 has an inner diameter of about 0.4 mm to about 2 mm, preferably about 1 mm.

FIGS. 4–7 illustrate an alternative embodiment of a system for delivering hemostasis promoting material in which a hydration chamber 312 is connected to a side port 320 of an introducer sheath 310. The vent tube 326 is connected to another port of the side port 320. The stop cock 322 is movable between an open delivery position shown in FIG. 4 and a closed bleed back position shown in phantom in FIG. 4. In the closed bleed back position, bleed back is allowed through the vent tube 326. In the open delivery position the hemostasis promoting material is delivered from the hydration chamber 312 to the introducer sheath. As in the embodiment described above in connection with FIGS. 1–3, a syringe 318 is coupled to and decoupled from a hydration chamber 312 by coupler 316.

Figure 7:
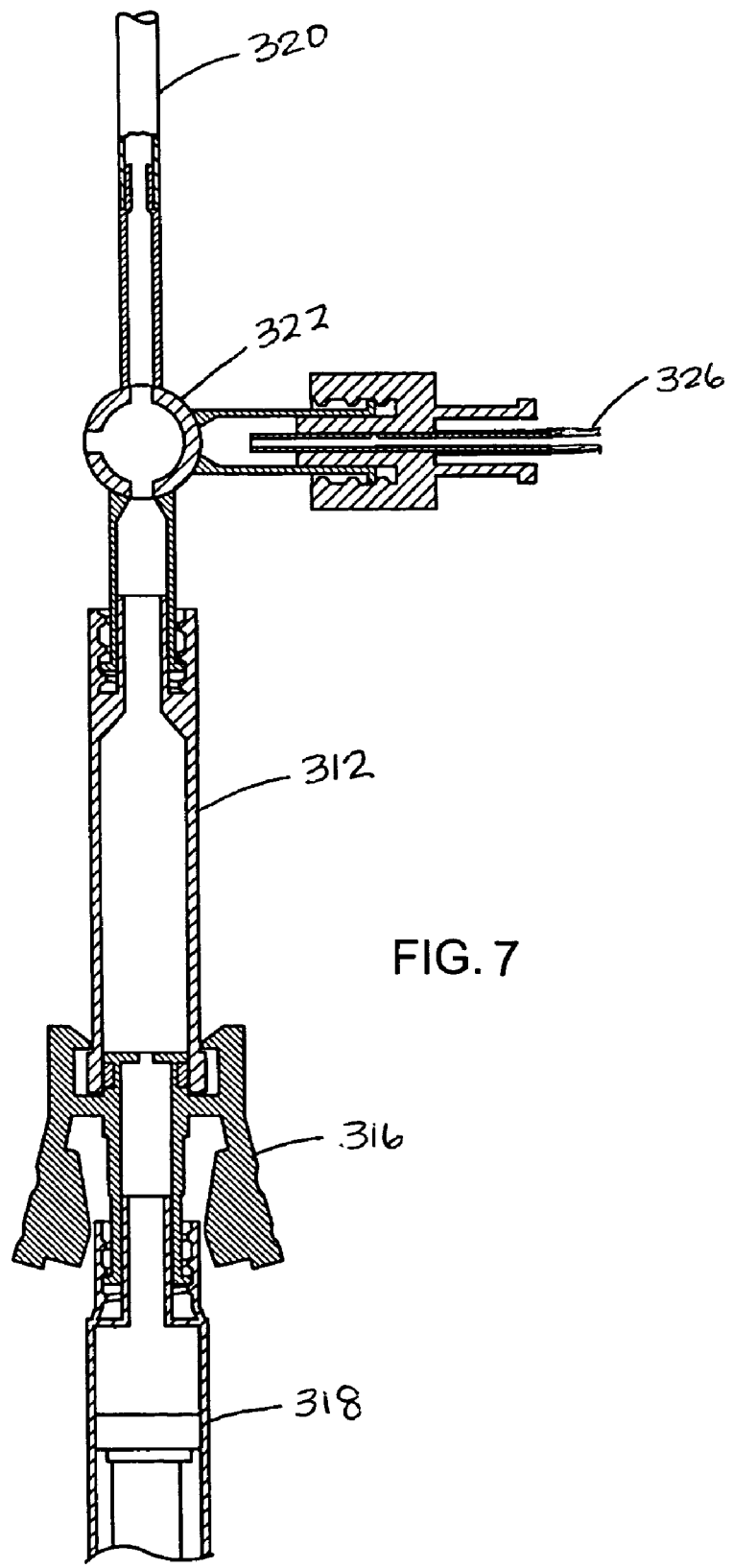
FIG. 7 is a side cross sectional view of a portion of the system of FIG. 5 including an exhaust valve, a hydration chamber, and a syringe.

As shown in the cross sectional view of FIG. 7, when the stop cock 322 is in the open delivery position, the hemostasis promoting material will pass from the hydration chamber 312 through the stop cock 322 and the side port 320 and into the introducer sheath 310 for delivery to the blood vessel puncture site.

Figure 6:
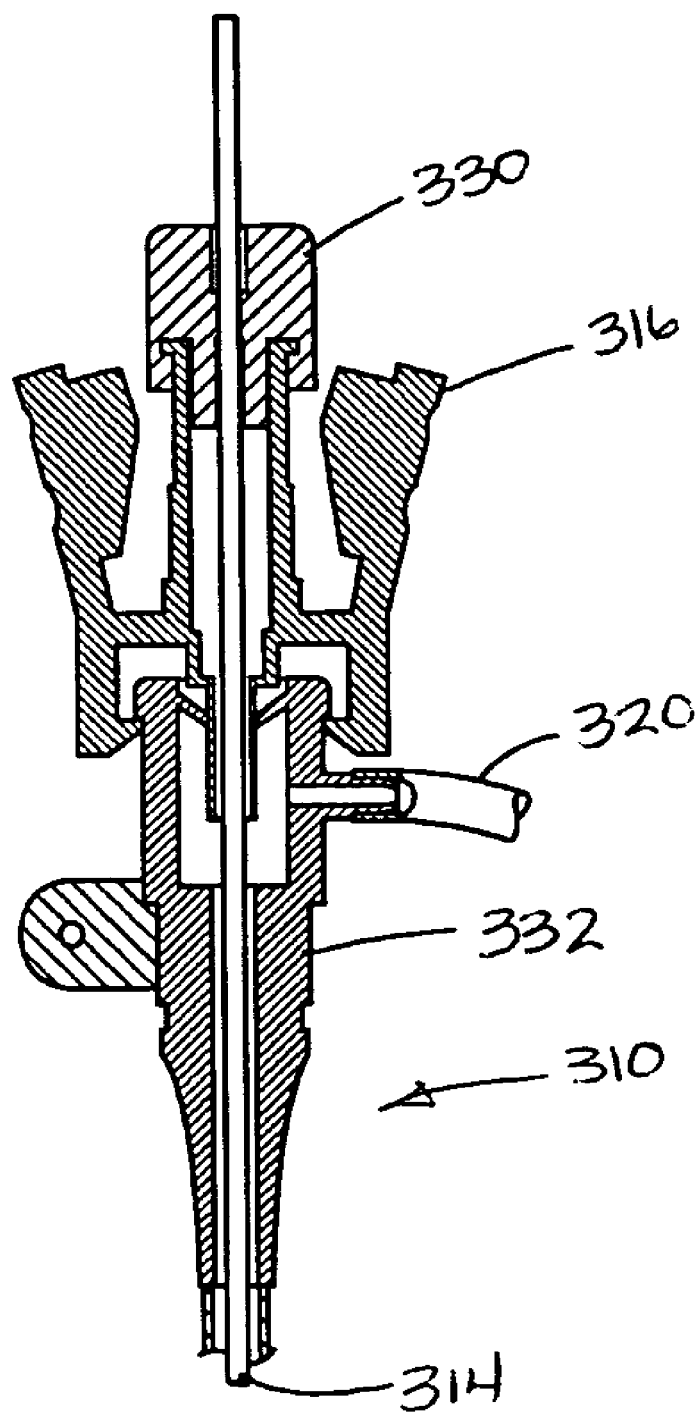
FIG. 6 is a side cross sectional view of a portion of the system of FIG. 5 including a proximal end of the introducer sheath and control tip.

FIG. 6 illustrates the connection of the control tip 314 to a proximal plug 330 which is connectable by a coupler 316 to the hub 332 of the introducer sheath 310. The hemostasis promoting material is delivered through the side port 320 of FIG. 6 and into the hub 332 of the introducer sheath 310 and then is delivered through the introducer sheath to the puncture site.

Figure 8:
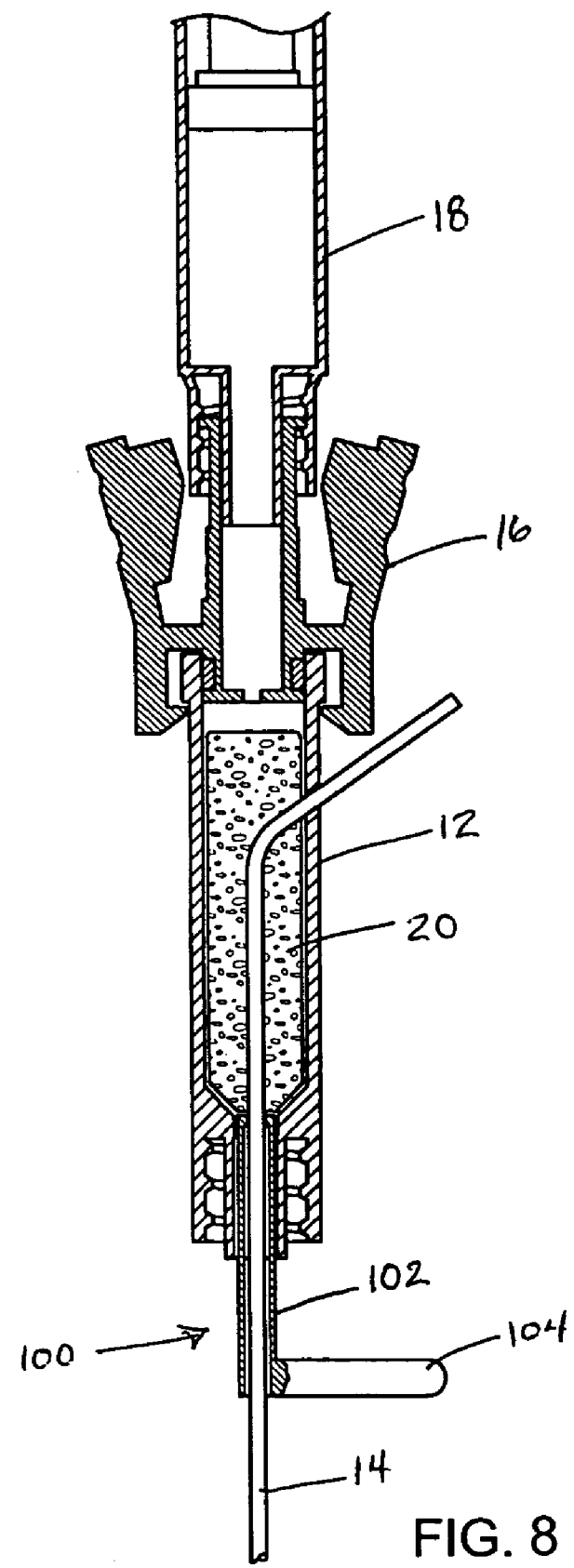
FIG. 8 is a side cross sectional view of a portion of the system of FIG. 1 with a pledget of hemostasis promoting material positioned in the hydration chamber.
Figure 9:
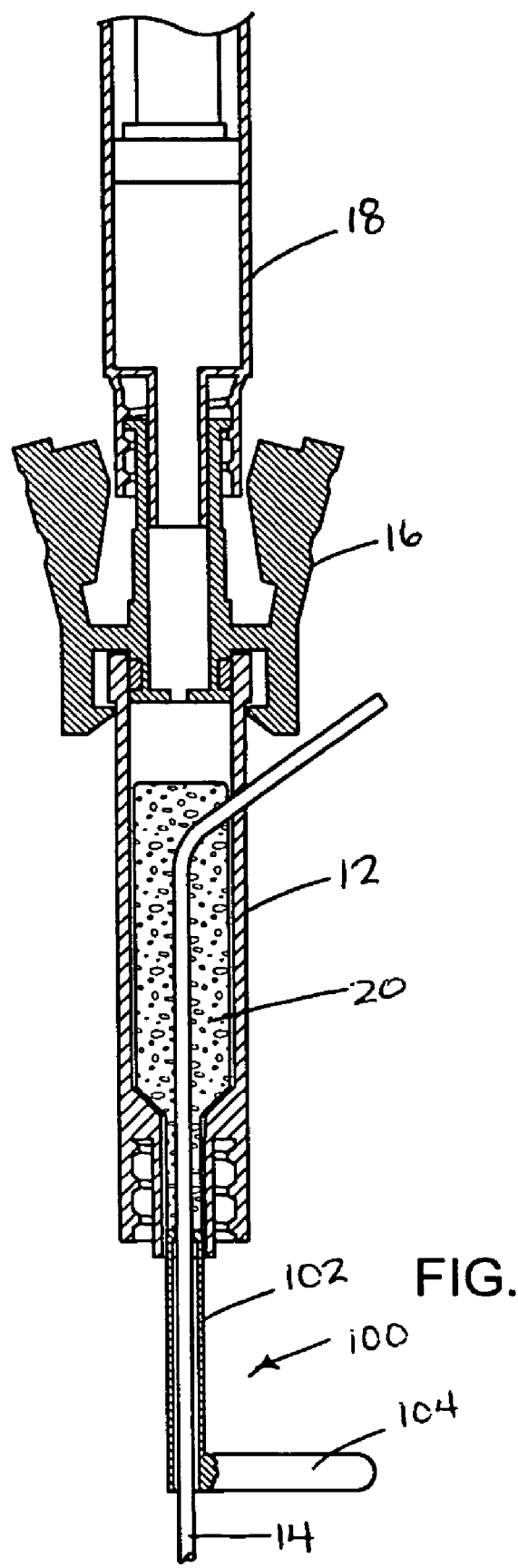
FIG. 9 is a side cross sectional view of a portion of the system of FIG. 1 with the sponge hydrated and advanced in preparation for delivery.

FIGS. 8–15 illustrate the preparation and use of the system for delivering hemostasis promoting material to a blood vessel puncture site. Although FIGS. 8–15 illustrate the procedure which is used with the embodiment of FIGS. 1–3, a similar procedure would be used with the other embodiments described below. FIGS. 8 and 9 illustrate the hydration and staging of a pledget 20 of sponge material in the hydration chamber 12. Once the pledget 20 is inserted into the hydration chamber 12 and the coupler 16 and syringe 18 have been connected to the proximal end of the hydration chamber, the pledget is ready to be hydrated and staged. For the staging procedure a staging tube 100 is used to position a distal end of the pledget 20 and prevent the pledget from being expelled from the hydration chamber 12. The staging tube 100 includes a tube 102 having a longitudinal slit (not shown) and preferably including a handle 104. The staging tube 100 uses a longitudinal slit to allow the staging tube to be mounted onto the shaft of the control tip 14 since the staging tube 100 will not fit over the enlarged distal end 40 of the control tip. Once the staging tube 100 is placed over the shaft of the control tip 14, it is advanced into the distal end of the hydration chamber 12 to the first position shown in FIG. 8. In the position illustrated in FIG. 8 saline or other fluid is injected at high pressure into the hydration chamber 12 by the syringe 18 to hydrate the pledget 20. The staging tube 100 is then moved to the position illustrated in FIG. 9 and additional fluid is injected by the syringe 18 to advance the pledget 20 into the distal end of the hydration chamber.

It should be noted that in embodiments of the invention employing a vent tube in a hydration chamber, the pledget 20 should be staged with a distal end of the pledget positioned proximally of the inlet to the vent tube to prevent the pledget from blocking the bleed back vent. Once the pledget 20 has been hydrated and staged at a desired position in the hydration chamber 12, the hemostasis promoting material delivery system is ready to deliver the pledget to the puncture site.

Figure 10:
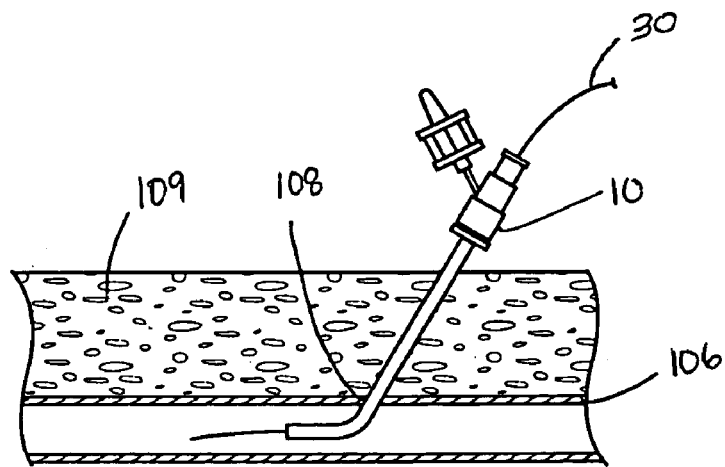
FIG. 10 is a side cross sectional view of a blood vessel puncture site with an introducer sheath and guidewire positioned in the blood vessel puncture.

FIG. 10 illustrates a blood vessel 106 with a puncture 108 and overlying tissue 109. In FIG. 10, the introducer sheath 10 and a guidewire 30 are in position in the blood vessel puncture 108 following an intravascular procedure.

Figure 11:
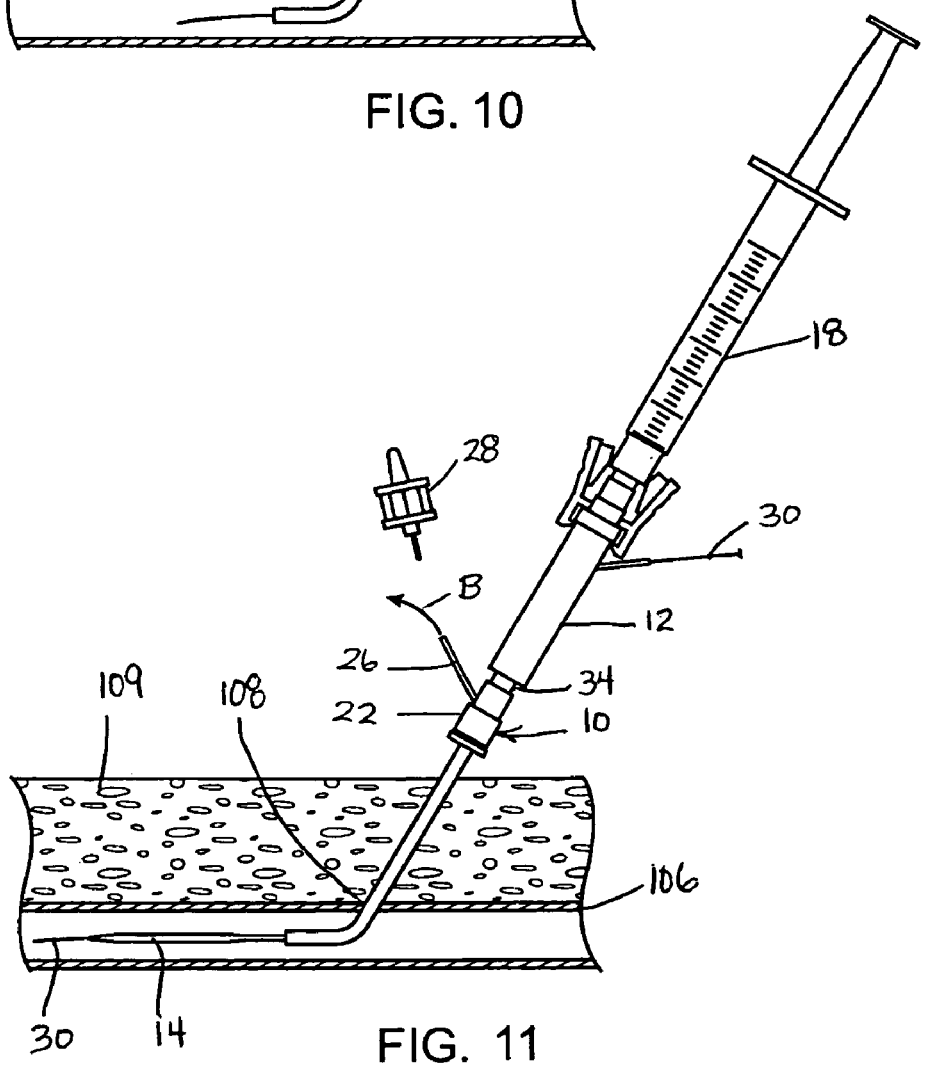
FIG. 11 is a side cross sectional view of the blood vessel puncture site with the hemostasis promoting material delivery system connected to the introducer sheath and bleed back visible from the vent tube.

In the step illustrated in FIG. 11, the control tip 14 has been inserted over the guidewire 30 and into the introducer sheath 10 and the distal end 34 of the hydration chamber 12 has been connected to the hub 22 of the introducer sheath. The vent cap 28 is then removed from vent tube 26 and the spurt of blood B called bleed back is observed from the vent tube.

Figure 12:
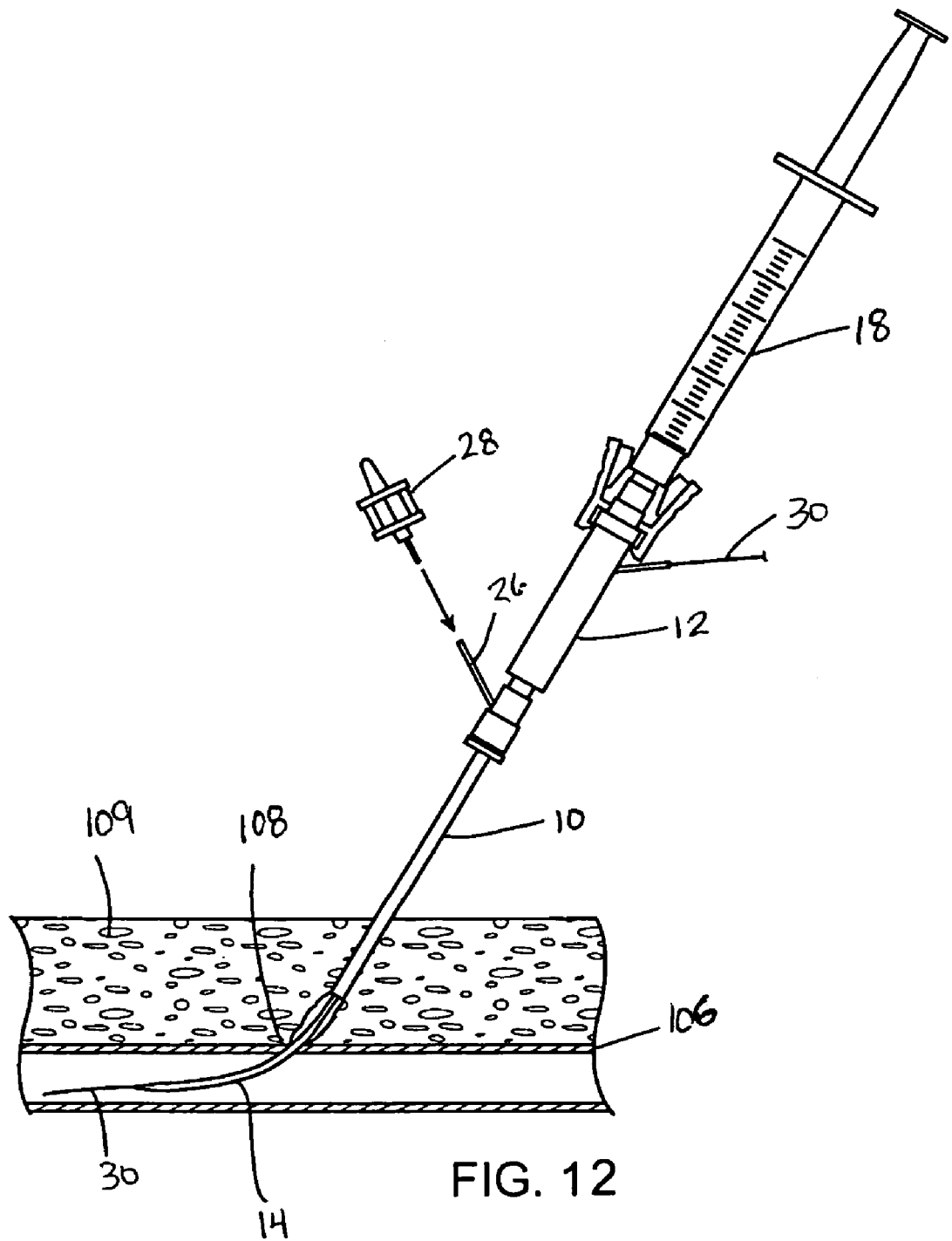
FIG. 12 is a side cross sectional view of the blood vessel puncture site with the hemostasis promoting material delivery system and introducer sheath withdrawn to a desired position for delivery of the hemostasis promoting material.

In the next step illustrated in FIG. 12, the combination of the introducer sheath 10, the hydration chamber 12, and the control tip 14, is slowly withdrawn from the puncture site until bleed back is no longer visible from the vent tube 26. When bleed back is no longer present this indicates that the enlarged distal end 40 of the control tip 14 is located in the blood vessel puncture 108 and is preventing blood from passing through the blood vessel puncture and into the introducer sheath 10.

Figure 13:
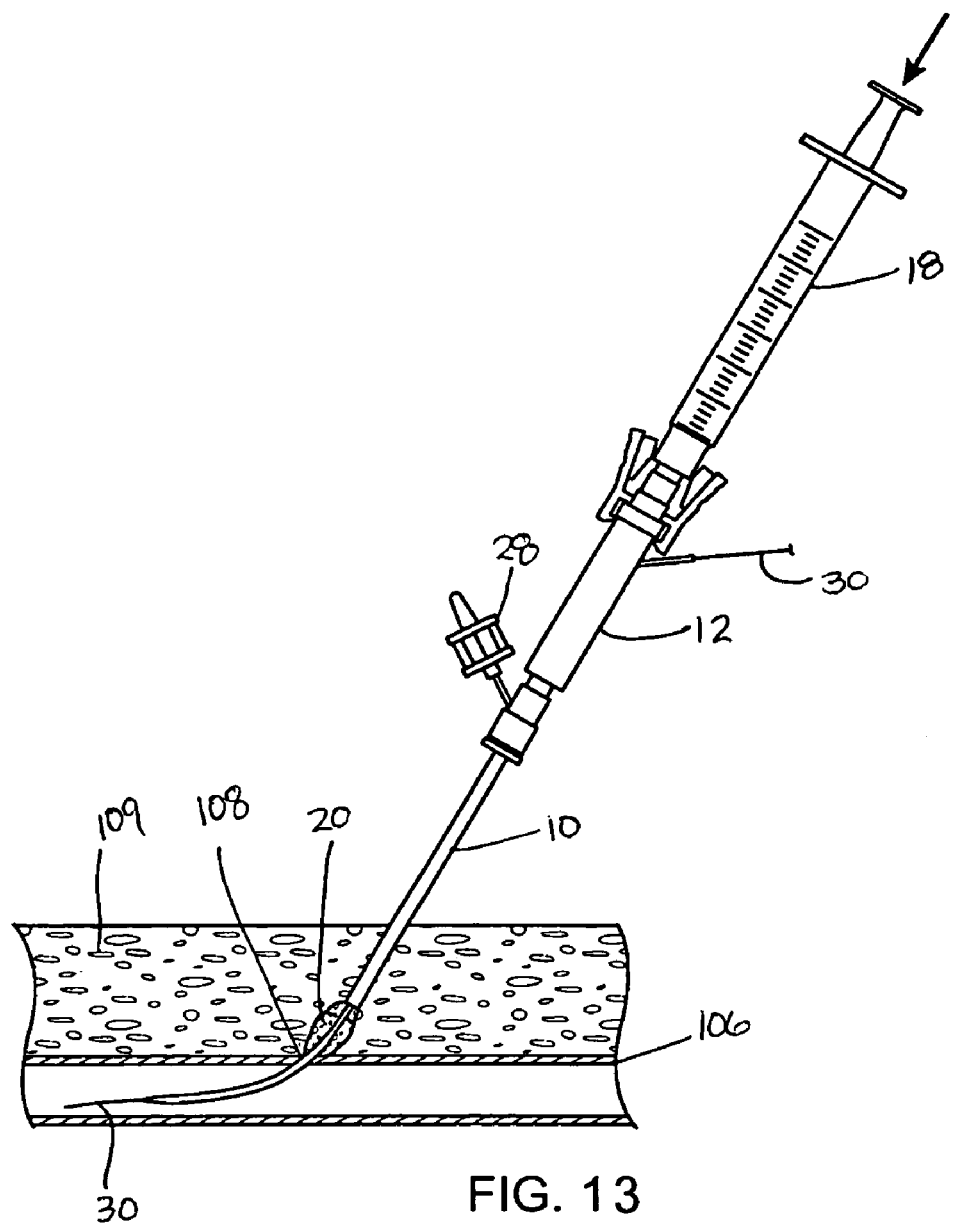
FIG. 13 is a side cross sectional view of the blood vessel puncture site with the hemostasis promoting material delivered to the blood vessel puncture site by fluid pressure.

FIG. 13 illustrates a step of injecting the hemostasis promoting material or pledget 20 to the blood vessel puncture site by fluid pressure applied by the syringe 18. The hemostasis promoting material substantially fills the tissue tract at a space between the puncture in the blood vessel and the location of a distal end of the introducer sheath 10. The pledget material, once delivered, rapidly expands to fill the tissue tract and promotes hemostasis of the blood vessel puncture.

Figure 14:
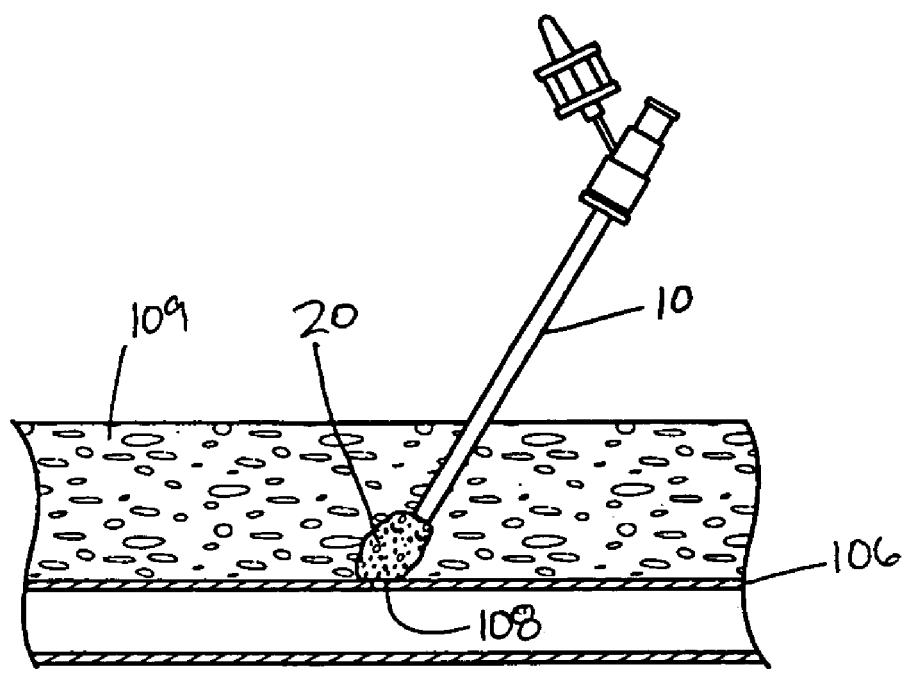
FIG. 14 is a side cross sectional view of the blood vessel puncture site with the hemostasis promoting material delivery system and guidewire removed from the introducer sheath.
Figure 15:
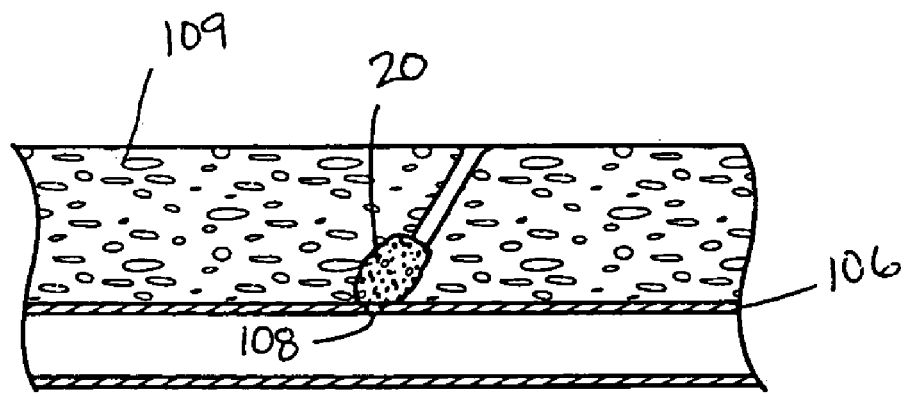
FIG. 15 is a side cross sectional view of the blood vessel puncture site with the introducer sheath withdrawn.

As shown in FIG. 14, the hydration chamber 12, the control tip 14, and the guidewire 30 are then removed from the puncture site with the introducer sheath 10 held in place to stabilize the hemostasis promoting material 20 during removal of the remaining structures. The introducer sheath 10 is then removed leaving the hemostasis promoting material in the tissue tract as shown in FIG. 15. Alternatively, the hydration chamber 12, control tip 14, guidewire 30, and introducer sheath 10 may be withdrawn together from the puncture site.

FIGS. 16, 16a, 16b and 16c illustrate another alternative embodiment. This embodiment includes a pledget handling system 400 for hydrating, staging and delivering a pledget 20. The pledget handling system 400 includes a body 402 which includes a substantially cylindrical section 404, sized to fit between the thumb 411 and forefinger 410, and two end sections 406 and 408 which substantially close the ends of the cylindrical section 404. A valve 412 is mounted in the body 402, and the valve 412 includes a rotatable control member 414 enclosed in a housing 416, and a control lever 418 is connected to the control member 414 to permit a user to rotate the control member 414. The control member 414 comprises a solid portion 470 which is substantially cylindrical, and a port 472 is formed through the solid portion 470. A relief, shown as a semi-cylindrical cut-out, 474 is formed in the edge of the solid portion 470. The control lever 418 is includes detents (not shown) which provide audible and tactile indication in the form of a clicking sound and feel to notify a user that the lever has moved from one position to another. The distal end of the valve 412 is connected to a coupling member 422 which permits coupling to a proximal hub of an introducer sheath (not shown). The proximal hub and introducer sheath are substantially the same as the proximal hub 332 and introducer sheath 310 shown in FIG. 4. A bleed back vent 420 is connected to valve 412.

A control tip 424 extends through the coupling member 422, and the proximal end of the control tip 426 is connected to the cylindrical section 404. The distal end of the control tip 424 is not shown and is substantially the same as the distal end of control tip 14 discussed above. The proximal end of valve 412 is connected to an elongated staging chamber 430 comprised of a hose 437, which is partially contained within the body 402 and forms an S shape. A first connector 432 is connected to the staging chamber 430 and protrudes from the end section 406 of body 402. Alternatively, instead of connector 432 a second connector 434 can be connected to the staging chamber 430 to extend through the cylindrical section 404. The connectors 432 and 434 are substantially the same and are constructed to permit a user to couple the distal end of the hydration chamber 312 in fluid flow communication with the staging chamber 430. The connectors 432 and 434 each include a one-way valve 436, but alternatively, instead of the one-way valves 436, manually operated valves such as gate valves or stop cocks can be used. The proximal end of the hose 437 is connected to a syringe 439, which is mounted to the body 402.

Figure 16:
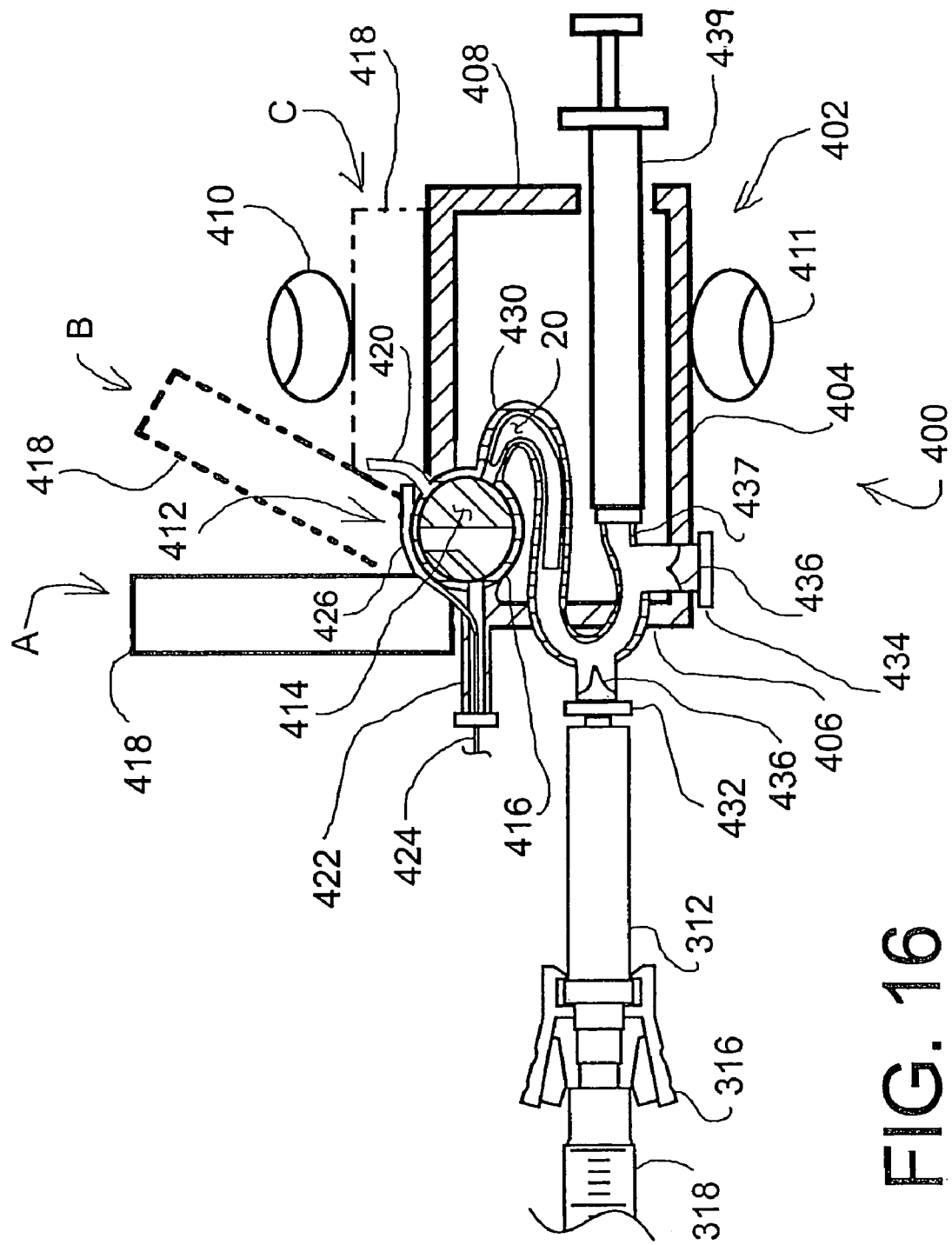
FIG. 16 is an alternative embodiment of a system for delivering hemostasis promoting material to a blood vessel puncture site by fluid pressure.

The operation of the embodiment shown in FIG. 16 is as follows. The hydration chamber 312 is supplied to the user containing a dry pledget 20, and pre-attached and the user then connects the hydration chamber 312 to connector 432 or 434. The user fills a syringe 318 with fluid (e.g. 3 or 4 cc's) and then connects syringe 318 to the hydration chamber 312. The user then uses the syringe 318 to push fluid into the staging chamber 430 and the delivery syringe 439 and fill the staging chamber 430 and delivery syringe 439, (which requires about 1 cc of fluid.)

Figure 16A:
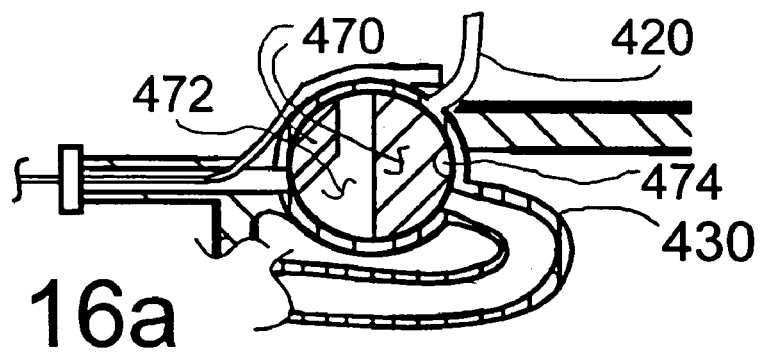
FIG. 16a is a detail of the embodiment shown in FIG. 16 illustrating the operation thereof.
Figure 16B:
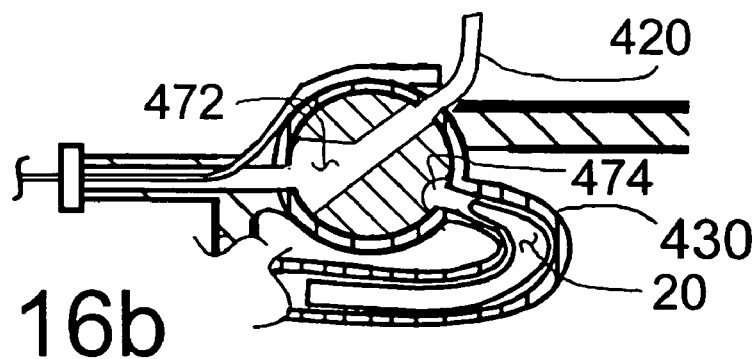
FIG. 16b is another detail of the embodiment shown in FIG. 16 illustrating the operation thereof.
Figure 16C:
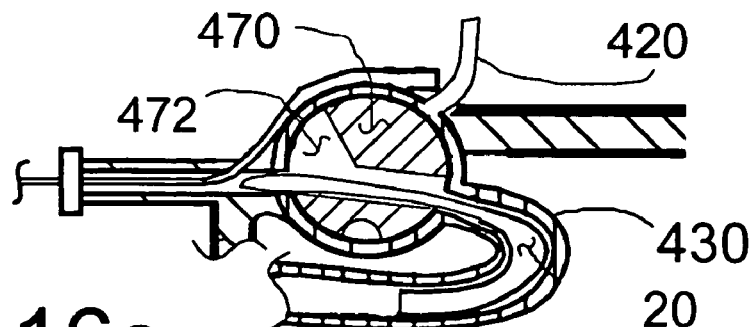
FIG. 16c is another detail of the embodiment shown in FIG. 16 illustrating the operation thereof.

During the steps above the control lever is in position A shown in solid lines in FIG. 16 so that the valve 412 is in the closed position illustrated in FIG. 16 and FIG. 16a. The user then uses the syringe 318 to apply fluid pressure to hydrate the pledget in the hydration chamber 312. After hydrating the pledget, the user then moves the control lever 418 to position B which causes the rotatable member 414 to rotate to the staging position (FIG. 16b.) It should be understood that the valve provides an audible and tactile click to notify the user that the valve has engaged in the staging position. In the staging position the valve permits a low rate of flow through the cut-out 474 and out of valve 412 via a vent, not shown, but cut-out 474 is sufficiently small so as not to permit passage of the pledget. The pledget 20 travels from the hydration chamber 312 into the staging chamber 430 and to a position adjacent the valve 412, as shown in FIG. 16b. At this time the pledget 20 is staged and the system is ready for placement (ready for delivery).

The user then removes the syringe 318 and staging chamber 312 from connector 432 or 434 and places the control tip 424 into an introducer sheath 10 which is already in the patient as previously discussed. The user then moves the control tip in the distal direction and checks for bleed back from the bleed back vent 420 to properly position the control tip as discussed above. The user then grasps the pledget handling system 400 with the thumb 411 and forefinger 410 as shown in FIG. 16 and rotates the lever 418 to position C. This causes the control member 414 to rotate to a position in which full flow is permitted between the proximal and distal sides of the valve 412. With the other hand the user applies fluid pressure with syringe 439 which causes the pledget to pass through the valve 412 and the introducer sheath 10 and be placed in the patient substantially as shown and described above in connection with FIGS. 13–15. It should be understood that because the coupling member rigidly connects the introducer sheath and the pledget handling system 400, the user can easily use one hand to operate the lever 418 while holding the introducer sheath steady.

Certain aspects of the staging chamber 430 should be understood. The length of the staging chamber 430 should be greater than or equal to the length of the pledget 20. The S-shaped configuration of the staging chamber 430 facilitates a device length that is shorter than one having a straight stager. Staging position B is also the position in which the user determines bleedback wherein blood flows out of the coupling member 422, through valve 412 and out bleedback vent tube 420.

Although the present invention has been described and illustrated with bleed back provided between the introducer sheath 10 and the control tip 14, an alternative way of obtaining bleed back involves providing a hole 438 in the control tip and bleed back through the internal lumen of the control tip. According to this alternative bleed back system, a bleed back hole 438 is provided in the enlarged distal end 40 of the control tip 14 at a location close to the proximal end of the enlarged portion. The bleed back hole 438 communicates with the lumen of the control tip body and allows bleed back to be viewed at the proximal end 44 of the control tip which extends out of the side wall of the hydration chamber 12. A system according to this design is taught in U.S. patent application Ser. No. 09/859,682, filed May 18, 2001, which was published May 23, 2002 as publication number US 2002/0062104 A1.

It is preferred that the distance d between the distal end of the introducer sheath and the enlarged distal end 40 of the control tip 14 in each of the foregoing embodiments be selected so that the point at which bleed back stops is the desired delivery location for delivering the hemostasis promoting material to the blood vessel puncture. Alternatively, the introducer sheath 10, hydration chamber 12, and control tip 14 may be withdrawn an additional predetermined amount to the desired delivery location after bleed back stops.

The system discussed above as taught in U.S. patent application Ser. No. 09/859,682, filed May 18, 2001, can be susceptible to certain problems in that blood can leak between the edges of the blood vessel puncture 108 and the enlarged distal end of the control tip 40 and flow through the introducer sheath 10. If such leakage occurs it can be difficult for the user to conclusively determine when bleedback stops and starts, thus making positioning of the device difficult. The following alternative embodiments can reduce or eliminate this problem.

The alternative embodiments shown in FIGS. 17–21 include a flexible seal around the control tip 14 which is sufficiently flexible and resilient to deform to fit through the introducer sheath and then expand upon emerging from the introducer sheath to prevent the leakage of blood between the edges of the puncture 108 and the enlarged end of the control tip 40 and through the introducer sheath. In FIG. 17 a flexible seal 440 includes a plurality of cylindrically shaped ridges 442 connected to each other by cylindrically shaped sections 444. The upper and lower ends of the seal 440 fit tightly to the enlarged distal end 40 of the control tip 14, and the diameters of the ridges 442 are larger than the inside diameter of the introducer sheath 10, and preferably greater than or equal to the outside diameter of the sheath 10. Thus, when enlarged distal end 40 of the control tip 14 is pushed through the introducer sheath 10, the ridges 442 are compressed to slide through the sheath 10, and when the ridges 442 emerge from the distal end of the introducer sheath 10 the ridges expand to have a diameter larger than the inside diameter of the introducer sheath 10, as shown in FIG. 17. Accordingly, when the enlarged distal end of the control tip emerges distally from the distal end of an introducer sheath already positioned within the blood vessel lumen, blood can flow into the sheath to be observed by the user. The sheath and control tip are withdrawn together until the ridges 442 emerge from the introducer sheath and are positioned within the blood vessel puncture 108. The ridges block the flow of blood from the blood vessel puncture into and through the introducer sheath. Moreover, as the ridges 442 emerge from the end of the introducer sheath 10 their rapid expansion causes a slight vibration through the control tip 14 to provide tactile feed back to the user indicating that the ridges have emerged. Also, it should be noted that the flexible nature of the ridges 442 facilitates their compression and removal through the sheath 10.

In the embodiment shown in FIG. 18 the flexible seal 440 comprises a conical member 446 connected to a cylindrical member 448. The cylindrical member 448 includes a cylindrical slot 450 in the interior thereof to cooperate with a raised cylindrical section 452 on the control tip 14 to keep the flexible seal in a fixed position along the length of the control tip 14. The conical member 446 is hollow and flexible to be easily pushed through the introducer sheath 10 and provide a fluid-tight seal within the vessel puncture and later easily removed through the sheath 10.

In the embodiment shown in FIG. 19 the control tip 14 includes a cylindrical slot 460 and the flexible seal 440 comprises a flexible member shaped like an O-ring gasket but having longer and more tapered edges than those of an O-ring.

In the embodiment in FIG. 20 the flexible seal 440 includes an upper, conical portion 462 having a plate-shaped portion 464 around the periphery thereof. The plate-shaped portion 464 is shaped like a dinner plate in that the outside edge is somewhat higher than the more central portion. This shape can be useful in allowing the flexible seal 440 to slide from the proximal toward the distal end of the introducer sheath while causing it to lock in a fixed position against the inner surfaces of the puncture 108 under pressure of blood from the blood vessel. As in the FIG. 18 embodiment the FIG. 20 embodiment includes a cylindrical slot 450 in the interior thereof to cooperate with a raised cylindrical section 452 on the control tip 14 to keep the flexible seal in a fixed position along the length of the control tip 14.

The embodiment in FIG. 21 is similar to the embodiment in FIG. 20, except that in the FIG. 21 embodiment a cylindrical slot 466 is formed in the interior of the seal 440 and the slot is filled with glue to glue the seal 440 to the control tip 14. It should also be understood that in this embodiment the periphery of the plate-shaped part 464 can flex upward and downward. This shape can be useful in allowing the flexible seal 440 to slide from through the introducer sheath either from the proximal toward the distal end or in the other direction.

The embodiment shown in FIG. 22 is similar to the embodiment shown in FIG. 21. However, the FIG. 22 embodiment includes a bleed back hole 438 formed in the control tip 14 and a bleed back port 476 formed in the flexible seal 441.

Figure 24:
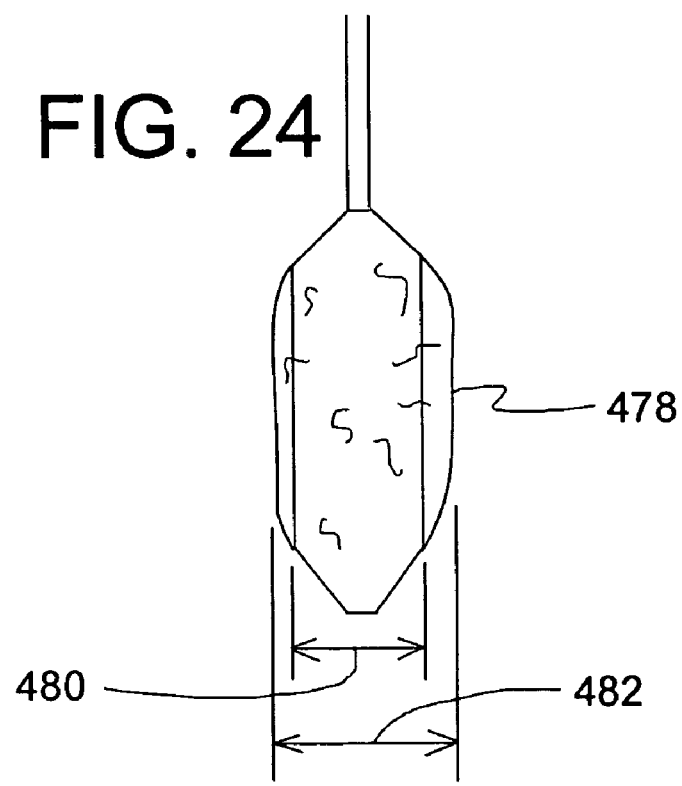
FIG. 24 is an alternative embodiment.
Figure 25:
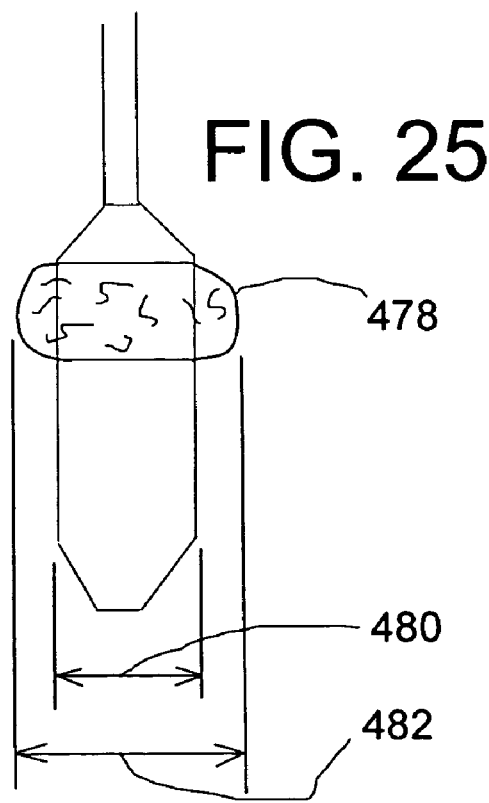
FIG. 25 is an alternative embodiment.

FIGS. 23–25 illustrate collapsable and expandable foam or expandable polymer regions on a control tip. FIG. 23 shows a conical tip with a proximal foam region 478 having an insertion diameter 480 less then or equal to the internal diameter of the sheath and an expanded diameter 482 greater than or equal to the outside diameter of the sheath. In this way the control tip can collapse (or be pre-collapsed) to pass through the sheath and into the blood vessel, and expand to a diameter greater than or equal to the size of the hole created by the sheath outside diameter. In this way, maximum puncture control can be achieved.

Alternative embodiments are shown in FIGS. 24 and 25 and other designs are possible. The foam may be non-absorbable, such as polyurethane foam, or may be absorbable, such as gelatin or collagen sponge. Further, the foam may be collapsed radially by the user to the sheath diameter as it is inserted into the sheath. It thereafter freely expands to the expanded diameter once inside the lumen of the blood vessel. In this way, it will provide maximum control of the puncture when positioned within the puncture, while still accommodating withdrawal through the sheath. Any of the embodiments shown in FIGS. 23–25 can be housed within an insertion aid which pre-collapses them to a diameter smaller than the expanded diameter and preferably less than or equal to the inside diameter or less than or equal to the insertion diameter. Any of the collapsible control tips can be coated with an absorbable capsule (e.g. gelatin or mannitol) in an insertion configuration to facilitate easy insertion, rapid capsule dissolution once in the lumen, and expansion of the collapsible member to the expanded diameter. Expansion may be driven by the elastic memory of the material, i.e. as a urethane foam pad or elastomer recovers when released from constraint. Expansion may be triggered by fluid absorption, i.e. a sponge swelling as it resorbs fluid. Expansion may be triggered by "heat memory". That is, an elastomer that has one shape at a first temperature (i.e. insertion diameter at room temperature) and a second radially larger shape at a second temperature (i.e. body temperature.)

Although the present invention has been described as a system for delivering hemostasis promoting material to a blood vessel puncture site which is delivered over a guidewire to the puncture site, the system may also be used without a guidewire in which case the lumen of the control tip may be omitted.

The entire system illustrated in the drawings may be provided in a kit or the parts may be provided individually for use with known introducer sheaths and syringes.

The hydration chamber 12 may be designed to be received interchangeably on one or more of a variety of different sheaths having different hub configurations. For example, some of the known introducer sheaths have hubs which include internal flanges, external flanges, internal threads, external threads, and/or locking detents. The hubs of some of these known sheaths are designed for connection to a correspondingly shaped dilator.

One example of a hemostasis promoting material for use in the systems of the present invention is commercially available Gelfoam from UpJohn. However, other forms of gelatin foam sponge may also be used which are modified from the commercially available Gelfoam to achieve reduced friction between the delivery system and the gelatin foam sponge. Once such modification is to change an amount of cross linking agent added to the gelatin to improve the delivery properties of the sponge.

For all of the embodiments of the control tip herein, during insertion, when the flexible seal 440 is in a collapsed state, the outer diameter of the central portion of the enlarged distal end 40 is between about 5 French and about 9 French, when used with a 5F to 9F sheath respectively. The expanded diameter of the flexible seal 440 shown in FIGS. 17, 18 and 19 are preferably greater than or equal to the outside diameter of the sheath 10. The expanded diameter of the flexible seal 440 shown in FIGS. 20, 21 and 22 are preferably significantly larger than the outside diameter of the sheath 10, and may range from about 3 mm to 10 mm depending upon the type of sheath used. The length of the enlarged control head, between the distal most end and the proximal end of the proximal tapered portion, is between about 1.5 inches (3.8 cm) and about 3 inches (7.6 cm), preferably between about 1.5 inches and about 2 inches (6.4 cm), and more preferably about 1.875 inches (4.8 cm). Control heads of these dimensions are well suited for controlling puncture sites as described herein, particularly puncture sites used during Seldinger-type vascular access.

The transverse cross sectional profile of the foregoing structures can be any desired shape, including square, oval, triangular, and preferably circular. The materials out of which the introducer sheaths, hydration chamber, control tip, and couplers are constructed are preferably selected to be relatively rigid and biocompatible, and more preferably are biocompatible polymers, biocompatible metals and metal alloys, and combinations thereof.

While the invention has been described in detail with reference to the preferred embodiments thereof, it will be apparent to one skilled in the art that various changes and modifications can be made and equivalents employed, without departing from the present invention.

What is claimed:

1. A system for delivering a pledget of hemostasis promoting material to a blood vessel puncture to facilitate hemostasis, the system comprising:
   an introducer sheath having a proximal end;
   a pledget handling system configured to receive a pledget of hemostasis promoting material, said pledget handling system having a connector configured to be connected to the proximal end of said introducer sheath, said pledget handling system comprising a valve to permit a user to control the staging and delivery of the pledget; and,
   a control tip coupled to said pledget handling system.

2. A system according to claim 1 wherein said pledget handling system comprises a body which is substantially cylindrical.

3. A system according to claim 1 wherein said pledget handling system comprises a delivery syringe.

4. A system according to claim 1 wherein said pledget handling system comprises a hose connected to provide fluid flow communication between said delivery syringe and said valve.

5. A system according to claim 4 wherein at least two connectors are connected to said hose to permit a user to connect a hydration chamber to said hose at a selected connector.

6. A system according to claim 1 wherein said valve is constructed to allow the user to control the flow of fluid from the distal end of said pledget handling system.

7. A system according to claim 1 wherein said valve is constructed to allow the user to control the hydration, staging and delivery of the pledget.

8. A method of promoting hemostasis of a blood vessel puncture using a pledget handling system which includes a valve, the method comprising:
   locating a pledget inside a hydration means;
   connecting said hydration means to said pledget handling system;
   setting the valve to a first position and hydrating the pledget in said hydration means;
   thereafter setting the valve to a second position and staging the pledget in said pledget handling system; and, thereafter setting the valve to a third position and delivering the pledget to promote hemostasis of the blood vessel puncture.

9. A method according to claim 8 wherein when the valve is in the first position the valve prevents fluid from flowing from the distal end of the pledget handling system.

10. A method according to claim 8 wherein the step of hydrating the sponge material includes applying pressurized fluid to the sponge material.

11. A method according to claim 8 wherein when the valve is in the second position the valve allows fluid to flow from the pledget handling system at a controlled rate while preventing the sponge material from traveling out of the pledget handling system.

* * * * *

UNITED STATES PATENT AND TRADEMARK OFFICE
CERTIFICATE OF CORRECTION

| | | |
|---|---|---|
| PATENT NO. | : 7,037,323 B2 | Page 1 of 1 |
| APPLICATION NO. | : 10/732441 | |
| DATED | : May 2, 2006 | |
| INVENTOR(S) | : Sing et al. | |

It is certified that error appears in the above-identified patent and that said Letters Patent is hereby corrected as shown below:

On the title page, item (56), line 27, page 2, under "U S PATENT DOCUMENTS", add:

--4,573,573      3/1986      Thomas C Krol--.

Signed and Sealed this

Twenty-seventh Day of March, 2007

JON W. DUDAS
*Director of the United States Patent and Trademark Office*